US006825167B1

(12) United States Patent
Yokoyama et al.

(10) Patent No.: US 6,825,167 B1
(45) Date of Patent: Nov. 30, 2004

(54) GENETIC MODIFICATION OF ENDOSTATIN

(75) Inventors: Yumi Yokoyama, St. Paul, MN (US); S. Ramakrishnan, North St. Paul, MN (US)

(73) Assignee: Regents of the University of Minnesota, Minneapolis, MN (US)

(*) Notice: Subject to any disclaimer, the term of this patent is extended or adjusted under 35 U.S.C. 154(b) by 161 days.

(21) Appl. No.: 09/825,765

(22) Filed: Apr. 4, 2001

Related U.S. Application Data

(63) Continuation-in-part of application No. 09/825,129, filed on Apr. 3, 2001.
(60) Provisional application No. 60/194,334, filed on Apr. 3, 2000.

(51) Int. Cl.$^7$ .............................................. A61K 38/00
(52) U.S. Cl. ........................ 514/12; 530/324; 530/402; 435/320.1
(58) Field of Search ........................... 514/12; 530/324, 530/402; 435/320.1

(56) References Cited

U.S. PATENT DOCUMENTS

| | | | |
|---|---|---|---|
| 5,767,071 A | 6/1998 | Palladino et al. | 514/11 |
| 5,792,845 A | 8/1998 | O'Reilly et al. | 536/23.1 |
| 5,854,205 A | 12/1998 | O'Reilly et al. | 514/2 |
| 2002/0193326 A1 * | 12/2002 | Sukhatme | |

FOREIGN PATENT DOCUMENTS

| | | | |
|---|---|---|---|
| EP | 0896003 | 2/1999 | C07K/14/75 |

OTHER PUBLICATIONS

Arap, W., et al., "Cancer Treatment by Targeted Drug Delivery to Tumor Vasculature in a Mouse Model", *Science*, 279, pp. 377–380, (Jan. 16, 1998).

Boehm, T., et al., "Antiangiogenic therapy of experimental cancer does not induce acquired drug resistance", *Nature*, 390, pp. 404–407, (Nov. 27, 1997).

Brooks, P.C., et al., "Insulin–like Growth Factor Receptor Cooperates With Integrin alphaVbeta5 to promote Tumor Cell Dissemination In Vivo", *Journal of Clinical Investigation*, 99 (6), pp. 1390–1398, (Mar. 1997).

Dawson, D.W., et al., "Pigment Epithelium–Derived Factors: A Potent Inhibitor of Angiogenesis", *Science*, 285, pp. 245–248, (Jul. 9, 1999).

Dhanabal, M., et al., "Endostatin Induces Endothelial Cell Apoptosis", *The Journal of Biological Chemistry*, 274 (17), pp. 11721–11726, (1999).

Ferrara, N., et al., "Molecular and Biological Properties of the Vascular Endothelial Growth Factor Family of Proteins", *Endocrine Reviews*, 13 (1), pp. 18–32, (1992).

Folkman, J., "Angiogenesis Inhibitors Generated by Tumors", *Molecular Medicine*, pp. 120–122, (1995).

Folkman, J., "What is the Evidencee That Tumors Are Angiogenesis Dependent?"*Journal of the National Cancer Institute*, 82 (1), pp. 4–6, (Jan. 3, 1990).

Friedlander, M. et al., "Definition of Two Angiogenic Pathways by Distinct alphav Integrins", *Science*, 270, pp. 1500–1502, (Dec. 1, 1995).

Kandel, J., et al., "Neovasculatization is Associated with a Switch to the Export of bFGF in the Multistep Development of Fibrosarcoma", *Cell*, 66, pp. 1095–1104, (Sep. 20, 1991).

O'Reilly, M.S., et al., "Antiangiogenic Activity of the Cleaved Conformation of the Serpin Antithrombin", *Science*, 285, pp. 1926–1928, (Sep. 17, 1999).

O'Reilly, M.S., et al., "Endostatin: An Endogeneous Inhibitor of Antiogenesis and Tumor Growth", *Cell*, 88, pp. 277–285, (Jan. 24, 1997).

Yokoyama, Y., et al., "Genetic Modification of Human Endostatin: RGD–Motif Potentiates Anti–Tumor Activity", *Proceedings of the American Association for Cancer Research*, 41, Abstract No. 3112, p. 488, (Mar. 2000).

* cited by examiner

*Primary Examiner*—Sheela J. Huff
(74) *Attorney, Agent, or Firm*—Schwegman, Lundberg, Woessner & Kluth, P.A.

(57) ABSTRACT

Chimeric polypeptides comprising a targeting moiety and an antiangiogeneic polypeptide are provided, as well as methods of using the chimeric polypeptides.

25 Claims, 10 Drawing Sheets

GENETIC MODIFICATION OF ENDOSTATIN

CROSS-REFERENCE TO RELATED APPLICATIONS

This application is a continuation in part application of U.S. application Ser. No. 09/825,129, filed on Apr. 3, 2001, which claims the benefit of the filing date of U.S. application Ser. No. 60/194,334 under 35 U.S.C. § 119(e) filed Apr. 3, 2000.

STATEMENT OF GOVERNMENT RIGHTS

The invention was made, at least in part, with grants from the Government of the United States (grant DAMD17-99-1-9564 from the United States Army and grant CA27469 from the National Institutes of Health). The Government may have certain rights to the invention.

BACKGROUND OF THE INVENTION

Establishing a new blood supply, known as neovascularization, is important for tumor growth and metastasis (Folkman 1990). Formation of blood vessels is a complex process involving endothelial cell proliferation, matrix degradation, migration, tube formation and maturation. Growth factors such as vascular endothelial growth factor (VEGF) and fibroblast growth factor (FGF) induce endothelial cell proliferation and migration (Ferrara et al. 1992; Kandel et al. 1991). In addition to growth factor receptor-mediated signaling, interaction between cell surface anchored integrins and extracellular matrix components constitute an additional pathway necessary for angiogenesis. In fact, recent studies have identified two cytokine mediated, integrin dependent angiogenic pathways. One of these pathways is associated with $\alpha_v\beta_3$ integrin, which selectively influences basic FGF (bFGF) mediated angiogenic signals (Friedlander et al. 1995). A second non-overlapping pathway is represented by crosstalk between $\alpha_v\beta_5$ integrin and protein kinase C (PKC) dependent growth factor mediated signaling (VEGF, bFGF, IGF, TNF-$\alpha$) (Friedlander et al. 1995; Brooks et al. 1997). Tumor angiogenesis can therefore be inhibited either by blocking the interaction between $\alpha_v\beta_3/\beta_5$ and arginine-glycine-aspartate (RGD) containing extracellular matrix or by interfering with angiogenic growth factors. A number of these strategies are currently under clinical development.

A number of proteolytic fragments of endogenous proteins and factors are capable of inhibiting angiogenesis (Folman 1995; Dawson et al. 1999). The former group of inhibitors includes angiostatin, encompassing kringle 1–4 of plasminogen, endostatin, a proteolytic fragment of a collagen type XVIII, and a fragment of antithrombin (Folman 1995; O'Reilly et al. 1997; O'Reilly et al. 1999). The molecular mechanism of action of angiostatic (antiangiogenic) proteins is not completely understood. Endostatin, for example, inhibits endothelial cell (EC) migration and induces apoptosis by modulating the antiapoptotic protein, BCL-2 (Dhanabal et al. 1999). A direct interaction with matrix metalloproteinases has also been suggested to be responsible for the antiangiogenic activity of endostatin (Kim et al. 2000). Endostatin treatment has been shown to inhibit solid tumor growth in a number of model systems (O'Reilly et al. 1997; Dhanabal et al. 1999; Boehm et al. 1997). O'Reilly et al. (1997) also reported that endostatin treatment resulted in complete regression of established tumors in some instances. However, the in vivo use of antiangiogenic proteins requires daily administration for prolonged periods of time. Improving the potency of these inhibitors would therefore significantly enhance the clinical use of these novel therapeutic molecules.

Therefore, what is needed are improved antiangiogenic proteins, i.e., proteins with increased potency so that higher efficacy may be achieved by lower doses.

SUMMARY OF THE INVENTION

The present invention provides a composition having a targeting moiety specific for endothelial cells linked to an antiangiogenic moiety. A "targeting moiety" as used herein is a molecule that facilitates the interaction and/or binding of the linked antiangiogenic moiety to endothelial cells. Preferably, the targeting moiety and the antiangiogenic moiety are polypeptides or peptides, which, when linked form a chimeric polypeptide. The term "chimeric polypeptide" refers to a protein that includes amino acid sequences or segments that are positioned or linked in a manner which does not normally occur in the native genome of a species. More preferably, the targeting moiety is a polypeptide or peptide derived from a particular extracellular matrix (ECM) polypeptide, such as human fibronectin. Fibronectin contains the tripeptide RGD (Arg-Gly-Asp), which is also found within most major types of matrix proteins. A "peptide" as used herein has fewer than 20 residues, e.g., fewer than 10 or fewer than 5 residues. Preferred targeting moieties bind to $\alpha_v\beta_3/\alpha_v\beta_5$ integrins, e.g., RGD is a motif found in molecules that bind $\alpha_v\beta_3$, and/or to $\alpha_5$ and/or $\alpha_v$ integrins, as endostatin may interact with $\alpha_5$ and/or $\alpha_v$ integrins as well (Rehn et al., 2001). Thus, preferred peptide or polypeptide targeting moieties are derived from RGD-containing molecules such as vitronectin, osteopontin bone sialoprotein, and disintegrins, as well as other molecules which are specific for $\alpha_v\beta_3$, e.g., echistatin, kistrin, integrelin, tirofiban, amifiban or xemolofiban, including anti-$\alpha_v\beta_3$ antibodies. Preferred targeting moieties include but are not limited to RGD, NGR, RGDNGR (SEQ ID NO:8), NGRRGD (SEQ ID NO:9), or tandom repeats of RGD, NGR, RGDNGR (SEQ ID NO:8), or NGRRGD (SEQ ID NO:9), or any combination thereof. Preferred polypeptide or peptide targeting moieties are less than about 100, more preferably less than about 50, even more preferably less than about 10, but at least 3, residues in length, and when linked to the antiangiogenic polypeptide yield a chimeric polypeptide that inhibits proliferation and/or migration of endothelial cells, attaches to endothelial cells, and/or inhibits tumor growth, and preferably is enhanced in these properties relative to the corresponding non-chimeric antiangiogenic polypeptide. In one embodiment of the invention, the targeting moiety is RGD.

The targeting moiety can be linked to the amino or the carboxyl terminus, or both, of the antiangiogenic polypeptide, e.g., by covalent bonding, and a different targeting moiety can be present at the amino terminus than at the carboxyl terminus. Preferred anti-angiogenic polypeptides are endostatin and angiostatin. For example, a chimeric endostatin, e.g., human endostatin genetically modified to include an RGD-motif at the amino or carboxyl terminus, is provided. As described hereinbelow, in vitro cell-binding studies showed that endothelial cells had enhanced binding to RGD-endostatin coated plates relative to native (unmodified) endostatin. The enhanced binding was completely blocked by anti $\alpha_v\beta_3$ antibody or RGD peptide. Endostatin-RGD was more potent in inhibiting bFGF-induced endothelial cell proliferation when compared to native endostatin. Moreover, RGD-modified endostatins were more potent in inhibiting endothelial cell migration when compared to native endostatin. RGD-containing endostatins were also more effective in inhibiting tumor growth in athymic nude mice. Further, a slow (sustained) release formulation comprising alginate beads and endostatin was very effective even at a fraction of the dose given in bolus injections. In particular, alginate beads containing the modified endostatin completely inhibited established ovarian cancers in athymic mice. Thus, the antiangiogenic activity of endostatin can be improved by adding an RGD-sequence.

The invention further provides a composition comprising a targeting moiety specific for endothelial cells linked to an antiangiogenic moiety and a pharmaceutically acceptable diluent. Also provided is a sustained release dosage form comprising a composition of the invention.

The invention also provides a recombinant polynucleotide encoding a chimeric polypeptide of the invention, host cells transformed with such a recombinant polynucleotide and the use of the composition, recombinant polynucleotide, e.g., in a recombinant virus, or transformed host cell of the invention, e.g., to inhibit or prevent undesirable endothelial cell proliferation and/or migration.

Further provided are methods to inhibit or prevent undesirable endothelial cell proliferation and/or migration. For example, a method of the invention involves contacting a mammalian endothelial cell with an amount of a composition of the invention effective to inhibit or prevent undesirable endothelial cell proliferation. Mammalian cells include primate cells such as human cells, rodent cells, e.g., mouse, hamster or rat, bovine cells, canine cells, feline cells, swine cells, equine cells, caprine cells, ovine cells and the like.

The present invention further provides therapeutic methods, which involve administering to a mammal having, or at risk of, a condition characterized by undesirable endothelial cell proliferation, an effective amount of a composition or a sustained release dosage form of the invention. A mammal includes a primate, human, rodent, canine, feline, bovine, ovine, equine, swine, caprine, bovine and the like. For example, a condition characterized by undesirable endothelial cell proliferation can be cancer, e.g., colon cancer, ovarian cancer, breast cancer or hematologic malignancies, diabetic retinopathy, rheumatoid arthritis, psoriasis, macular degeneration, restenosis, or eye disorders related to endothelial cell proliferation.

DETAILED DESCRIPTION OF THE INVENTION

Figure 1:
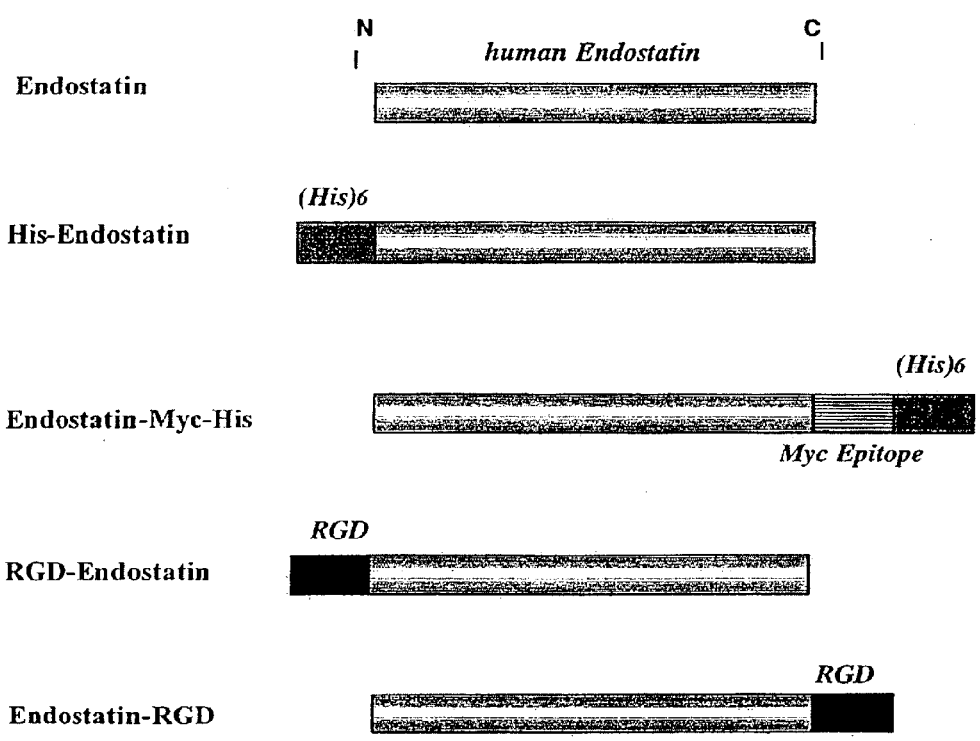
FIG. 1. Schematic of constructs prepared in the present invention.

Integrins are a large family of transmembrane receptors that bind to components of the extracellular matrix (ECM) and to other cell surface receptors. Integrins have been characterized as heterodimeric transmembrane glycoproteins, and attach cells to ECM proteins of the basement membrane or to ligands on other cells. Integrins contain large (α) and small (β) subunits of sizes 120–170 kDa and 90–100 kDa, respectively. Some integrins mediate direct cell to cell recognition and interactions. One of the most significant features of integrins is that they serve as transmembrane links between ECM molecules and the actin cytoskeleton. Certain peptide motifs have been reported in the literature to facilitate integrin binding, e.g., Arg-Gly-Asp (RGD) and Asn-Gly-Arg (NGR) (Arap et al., EP 0 896 003, and U.S. Pat. No. 5,767,071).

Since angiostatin and endostatin were identified in the mid 1990s, they have been the subject of intense clinical study and have entered Phase I clinical trials. The literature is replete with publications highlighting the antiangiogenic effects of each. See, for example, U.S. Pat. Nos. 5,792,845 and 5,854,205. One of the possible strategies to increase the potency of an antiangiogenic protein is to modify the protein. The abundant expression of $\alpha_v\beta_3/\beta_5$ integrins on tumor vascular endothelial cells offers an opportunity to target therapeutic compounds to endothelial cells by linking them to RGD-peptides (Arap et al. 1998). In fact, cyclic peptides containing the RGD-sequence itself are potent inhibitors of tumor angiogenesis and metastasis (Kumagai et al. 1991). Recent studies by Maeshima et al. (2000) showed that antiangiogenic proteins derived from the NC-1 domain of collagen IV α-3 chain (Tumstatin) could bind to $\alpha_v\beta_3$ integrins in an RGD independent manner. It is likely that RGD-dependent and -independent interactions with $\alpha_v\beta_3$ are involved in antiangiogenic activity.

I. Chimeric Polypeptides of the Invention and the Preparation Thereof

The invention provides a composition comprising a targeting moiety for endothelial cells, e.g., a moiety which binds to integrins on the surface of those cells, linked to an antiangiogenic polypeptide. The proliferation and/or migration of endothelial cells contacted with the composition of the invention is inhibited to a greater extent than the proliferation and/or migration of endothelial cells contacted with the antiangiogenic polypeptide alone. Moreover, the linked targeting moiety-antiangiogenic polypeptide preferably attaches to endothelial cells to a greater extent than the antiangiogenic polypeptide alone. Also, the administration of a composition of the invention to a mammal having or at risk of a condition characterized by undesirable endothelial cell proliferation or migration, e.g., neovascularization associated with tumor growth and/or late-stage metastatic disease, results in decreased endothelial cell proliferation or migration and/or decreased neovascularization. Thus, the antiangiogenic properties of the antiangiogenic polypeptide are enhanced by the targeting moiety.

Preferred targeting moieties bind to integrins on the surface of endothelial cells, and more preferably to $\alpha_v\beta_3/\beta_5$ integrins. In one embodiment of the invention, the targeting moiety is a peptide or polypeptide the sequence of which is derived from a protein present in ECM that binds integrins including, but not limited to, activated-leukocyte cell adhesion molecule, fibronectin, collagen, elastin, laminin, tenascin, fibrinogen, von Willebrand's factor, vitronectin, thrombospondin, osteopontin, or bone sialoprotein. A preferred targeting moiety is a peptide or polypeptide comprising RGD.

A number of naturally occurring proteins and other small molecules can inhibit angiogenesis. This group includes but is not limited to angiostatin, endostatin, and thrombospondin-1, as well as interferons (alpha, beta and gamma), platelet factor 4, prolactin 16 Kd fragment, anti-angiogenic antithrombin III, cartilage-derived inhibitor (CDI), CD59 complement fragment, fibronectin fragment, gro-beta, heparinases, heparin hexasaccharide fragment, human chorionic gonadotropin (hCG), interferon inducible protein (IP-10), interleukin- 12, kringle 5 (plasminogen fragment), 2-methoxyestradiol, placental ribonuclease inhibitor, plasminogen activator inhibitor, proliferin-related protein (PRP), retinoids, tetrahydrocortisol-S, transforming growth factor-beta (TGF-beta), vasculostatin, vasostatin (calreticulin fragment), tissue inhibitor of metalloproteinase-1 (TIMP-1), tissue inhibitor of metalloproteinase-2 (TIMP-2), and tissue inhibitor of metalloproteinase-3 (TIMP-3) (see for example the URL "www.nci.hih.gov/"). According to the National Cancer Institute, about 20 angiogenesis inhibitors are currently being tested in human trials. Most are in early phase I or II clinical (human) studies. Some are in or entering phase III testing. See URL "cancertrials.nci.nih.gov/news/angio/ table.html" for a list of angiogenesis inhibitors in clinical trials. These inhibitors include agents that block matrix breakdown, e.g., marimastat, COL-3, neovastat, and BMS-275291; agents that block angiogenesis activators, e.g., SU5416, SU6668, interferon α, anti-VEGF antibody; agents that directly inhibit endothelial cells, e.g., thalidomide; squalamine, endostatin; agents that inhibit endothelial-specific integrin signaling, e.g., EMD 121974; and others, e.g., CAI, interleukin-12, and IM862. Thus, it is also envisioned that any of these antiangiogenic moieties may be linked to a targeting moiety of the invention.

A. Recombinant Production of the Chimeric Polypeptide of the Invention

1. Sources, Isolation and Modification of the Polynucleotide Molecules Encoding Targeting Moieties and Antiangiogenic Polypeptides of the Invention Sources of nucleic acid from which a polynucleotide molecule encoding an antiangiogenic polypeptide or targeting polypeptide of the invention include RNA or DNA from any vertebrate source including genomic and cDNA libraries. By "polynucleotide" is meant a sequence of nucleotides including, but not limited to, RNA such as MRNA, cDNA, genomic DNA sequences and even synthetic DNA sequences. The term also includes sequences that include any of the known base analogs of DNA and RNA.

A polynucleotide encoding an antiangiogenic polypeptide or targeting polypeptide of the invention can be identified and isolated using standard methods, as described by Sambrook et al., Molecular Cloning: A Laboratory Manual, Cold Spring Harbor, N.Y. (1989). For example, reverse-transcriptase PCR (RT-PCR) can be employed to isolate and clone a preselected cDNA. Oligo-dT can be employed as a primer in a reverse transcriptase reaction to prepare first-strand cDNAs from isolated RNA which contains RNA sequences of interest, e.g., total RNA isolated from vertebrate or mammalian tissue. RNA can be isolated by methods known to the art, e.g., using TRIZOL™ reagent (GIBCO-BRL/Life Technologies, Gaithersburg, Md.). Resultant first-strand cDNAs are then amplified in PCR reactions.

"Polymerase chain reaction" or "PCR" refers to a procedure or technique in which amounts of a preselected fragment of nucleic acid, RNA and/or DNA, are amplified as described in U.S. Pat. No. 4,683,195. Generally, sequence information from the ends of the region of interest or beyond is employed to design oligonucleotide primers comprising at least 7–8 nucleotides. These primers will be identical or similar in sequence to opposite strands of the template to be amplified. PCR can be used to amplify specific RNA sequences, specific DNA sequences from total DNA, and cDNA transcribed from total cellular RNA, bacteriophage or plasmid sequences, and the like. See generally Mullis et al., Cold Spring Harbor Symp. Quant. Biol., 51, 263 (1987); Erlich, ed., PCR Technology, (Stockton Press, NY, 1989). Thus, PCR-based cloning approaches rely upon conserved sequences deduced from alignments of related gene or polypeptide sequences.

Primers are made to correspond to highly conserved regions of polypeptides or nucleotide sequences which were identified and compared to generate the primers, e.g., by a sequence comparison of genes related an antiangiogenic or targeting polypeptide. One primer is prepared which is predicted to anneal to the antisense strand, and another primer prepared which is predicted to anneal to the sense strand, of a polynucleotide molecule which encodes the preselected peptide or polypeptide.

The products of each PCR reaction are separated via an agarose gel and all consistently amplified products are gel-purified and cloned directly into a suitable vector, such as a known plasmid vector. The resultant plasmids are subjected to restriction endonuclease and dideoxy sequencing of double-stranded plasmid DNAs. Alternatively, isolated gel-purified fragments may be directly sequenced.

Once a desired polynucleotide is isolated, these same techniques may be employed to prepare recombinant DNA encoding the chimeric polypeptide of the invention.

As used herein, the terms "isolated and/or purified" refer to in vitro isolation of a polynucleotide, e.g., DNA, peptide or polypeptide molecule from its natural cellular environment, and from association with other components of the cell, such as nucleic acid or polypeptide, so that it can be sequenced, replicated, and/or expressed or otherwise analyzed for its properties. For example, an "isolated polynucleotide" is RNA or DNA containing greater than 9, preferably 36, and more preferably 45 or more, sequential nucleotide bases that encode at least a portion of a chimeric polypeptide of the invention, or a variant thereof, or a RNA or DNA complementary thereto, that is complementary or hybridizes, respectively, to RNA or DNA encoding the chimeric polypeptide, and remains stably bound under stringent conditions, as defined by methods well known in the art, e.g., in Sambrook et al., supra. Thus, the RNA or DNA is "isolated" in that it is free from at least one contaminating nucleic acid with which it is normally associated in the natural source of the RNA or DNA and is preferably substantially free of any other vertebrate or mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell.

As used herein, the term "recombinant nucleic acid" or "preselected nucleic acid," e.g., "recombinant DNA sequence or segment" or "preselected DNA sequence or segment" refers to a nucleic acid, e.g., to DNA, that has been derived or isolated from any appropriate source, that may be subsequently chemically altered in vitro, so that its sequence is not naturally occurring, or corresponds to naturally occurring sequences that are not positioned as they would be positioned in a genome which has not been transformed with exogenous DNA. An example of preselected DNA "derived" from a source, would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. See Lawn et al. (1981), and Goeddel et al. (1980). Therefore, "preselected DNA" includes completely synthetic DNA sequences, semi-synthetic DNA sequences, DNA sequences isolated from biological sources, and DNA sequences derived from RNA, as well as mixtures thereof. As used herein, the term "derived" with respect to a RNA molecule means that the RNA molecule has complementary sequence identity to a particular DNA molecule.

Polynucleotide molecules encoding amino acid sequence variants of a chimeric polypeptide of the invention are prepared by a variety of methods known in the art. These methods include, but are not limited to, isolation of a variant of the targeting polypeptide or antiangiogenic polypeptide from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the chimeric polypeptide.

Oligonucleotide-mediated mutagenesis is a preferred method for preparing amino acid substitution variants. This technique is well known in the art as described by Adelman et al. (1983). Briefly, DNA is altered by hybridizing an oligonucleotide encoding the desired mutation to a DNA template, where the template is the single-stranded form of a plasmid or bacteriophage containing the unaltered or native DNA sequence. After hybridization, a DNA polymerase is used to synthesize an entire second complementary strand of the template that will thus incorporate the oligonucleotide primer, and will code for the selected alteration in the DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. (1978).

The DNA template can be generated by those vectors that are either derived from bacteriophage M13 vectors (the commercially available M13mp18 and M13mp19 vectors are suitable), or those vectors that contain a single-stranded phage origin of replication as described by Viera et al (1987). Thus, the DNA that is to be mutated may be inserted into one of these vectors to generate single-stranded template. Production of the single-stranded template is described in Sections 4.2–4.41 of Sambrook et al., *Molecular Cloning: A Laboratory Manual* (Cold Spring Harbor Laboratory Press, N.Y. 1989).

Alternatively, single-stranded DNA template may be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of the peptide, and the other strand (the original template) encodes the native, unaltered sequence of the peptide. This heteroduplex molecule is then transformed into a suitable host cell, usually a prokaryote such as *E. coli* JM101. After the cells are grown, they are plated onto agarose plates and screened using the oligonucleotide primer radiolabeled with 32-phosphate to identify the bacterial colonies that contain the mutated DNA. The mutated region is then removed and placed in an appropriate vector for peptide or polypeptide production, generally an expression vector of the type typically employed for transformation of an appropriate host.

The method described immediately above may be modified such that a homoduplex molecule is created wherein both strands of the plasmid contain the mutations(s). The modifications are as follows: the single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thiodeoxyribocytosine called dCTP-($\alpha$S) (which can be obtained from the Amersham Corporation). This mixture is added to the template-oligonucleotide complex. Upon addition of DNA polymnerase to this mixture, a strand of DNA identical to the template except for the mutated bases is generated. In addition, this new strand of DNA will contain dCTP-($\alpha$S) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This oomoduplex molecule can then be transform ed into a suitable host cell such as *E. coli* JM101.

Other methods to prepare polynucleotide variants include DNA shuffling. DNA shuffling is a method to introduce mutations or rearrangements, preferably randomly, in a DNA molecule or to generate exchanges of DNA sequences between two or more DNA molecules, preferably randomly. The DNA molecule resulting from DNA shuffling is a shuffled DNA molecule that is a non-naturally occurring DNA molecule derived from at least one template DNA molecule. The shuffled DNA preferably encodes a variant polypeptide modified with respect to the polypeptide encoded by the template DNA, and may have an altered biological activity with respect to the polypeptide encoded by the template DNA. Strategies for such DNA shuffling are known in the art. See, for example, Stemmer, 1994; Stemmer, 1994; Crameri et al., 1997; Moore et al., 1997; Zhang et al., 1997; Crameri et al., 1998; and U.S. Pat. Nos. 5,605,793 and 5,837,458.

2. Expression Cassettes and Transformation

To prepare expression cassettes for transformation of cells, the recombinant DNA sequence o r segment may be circular or linear, double-stranded or single-stranded. Generally, the recombinant DNA sequence or segment is in the form of chimeric DNA, such as plasmid DNA, that can also contain coding regions flanked by control sequences which promote the expression of the recombinant DNA present in the resultant transformed cell.

As used herein, a "chimeric" vector or expression cassette means that a vector or cassette comprises DNA from at least two different species, or comprises DNA from the same species, which is linked or associated in a manner which does not occur in the "native" or wild type of the species. A "vector" is a replicon, such as a plasmid, phage, virus, or cosmid, to which another DNA segment may be attached so as to bring about the replication of the attached segment.

Aside from recombinant DNA sequences that serve as transcription units for a peptide or polypeptide, a portion of the recombinant DNA may be untranscribed, serving a regulatory or a structural function. For example, the recombinant DNA may itself comprise a promoter that is active in eukaryotic cells, or may utilize a promoter already present in the genome that is the transformation target. Many promoter elements well known to the art may be employed in the practice of the invention.

Other elements functional in the host cells, such as introns, enhancers, polyadenylation sequences and the like, may also be a part of the recombinant DNA. Such elements may or may not be necessary for the function of the DNA, but may provide improved expression of the DNA by affecting transcription, stability of the mRNA, or the like. Such elements may be included in the DNA as desired to obtain the optimal performance of the transforming DNA in the cell.

"Control sequences" is defined to mean DNA sequences necessary for the expression of an operably linked coding sequence in a particular host organism. A DNA "coding sequence" or a "sequence encoding" a particular polypeptide, is a DNA sequence which is transcribed and translated into a polypeptide in vitro or in vivo when placed under the control of appropriate regulatory elements. The boundaries of the coding sequence are determined by a start codon at the 5'-terminus and a translation stop codon at the 3'-terminus. A coding sequence can include, but is not limited to, procaryotic sequences, cDNA from eucaryotic mRNA, genomic DNA sequences from eucaryotic (e.g., mammalian) DNA, and even synthetic DNA sequences. A transcription termination sequence will usually be located 3' to the coding sequence.

The term DNA "control elements" refers collectively to promoters, ribosome binding sites, polyadenylation signals, transcription termination sequences, upstream regulatory domains, enhancers, and the like, which collectively provide for the transcription and translation of a coding sequence in a host cell. Not all of these control sequences need always be present in a recombinant vector so long as the desired gene is capable of being transcribed and translated.

A control element, such as a promoter, "directs the transcription" of a coding sequence in a cell when RNA polymerase binds the promoter and transcribes the coding sequence into MRNA, which is then translated into the polypeptide encoded by the coding sequence.

The control sequences that are suitable for prokaryotic cells, for example, include a promoter, and optionally an operator sequence, and a ribosome binding site. Eukaryotic cells are known to utilize promoters, polyadenylation signals, and enhancers.

"Operably linked" is defined to mean that the nucleic acids are placed in a functional relationship with another nucleic acid sequence. For example, DNA for a presequence or secretory leader is operably linked to DNA for a peptide or (polypeptide if it is expressed as a preprotein that participates in the secretion of the peptide or polypeptide; a promoter or enhancer is operably linked to a coding sequence if it affects the transcription of the sequence, or a ribosome binding site is operably linked to a coding sequence if it is positioned so as to facilitate translation.

Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accord with conventional practice.

The recombinant DNA to be introduced into the cells further will generally contain either a selectable marker gene or a reporter gene or both to facilitate identification and selection of transformed cells from the population of cells sought to be transformed. Alternatively, the selectable marker may be carried on a separate piece of DNA and used in a co-transformation procedure. Both selectable markers and reporter genes may be flanked with appropriate regulatory sequences to enable expression in the host cells.

Reporter genes are used for identifying potentially transformed cells and for evaluating the functionality of regulatory sequences. Reporter genes which encode for easily assayable proteins are well known in the art. In general, a reporter gene is a gene which is not present in or expressed by the recipient organism or tissue and which encodes a protein whose expression is manifested by some easily detectable property, e.g., enzymatic activity. Preferred genes include the chloramphenicol acetyl transferase gene (cat) from Tn9 of *E. coli*, the beta-glucuronidase gene (gus) of the uidA locus of *E. coli*, and the luciferase gene from firefly *Photinus pyralis*. Expression of the reporter gene is assayed at a suitable time after the DNA has been introduced into the recipient cells.

A "host cell" is a cell which has been transformed, or is capable of transformation, by an exogenous nucleic acid molecule.

A cell has been "transformed" by exogenous DNA when such exogenous DNA has been introduced inside the cell membrane. Exogenous DNA may or may not be integrated (covalently linked) into chromosomal DNA making up the genome of the cell. In procaryotes and yeasts, for example, the exogenous DNA may be maintained on an episomal element, such as a plasmid. With respect to eucaryotic cells, a stably transformed cell is one in which the exogenous DNA has become integrated into the chromosome so that it is inherited by daughter cells through chromosome replication. This stability is demonstrated by the ability of the eucaryotic cell to establish cell lines or clones comprised of a population of daughter cells containing the exogenous DNA. Preferred transformed host cells for implantation into a recipient mammal include transformed mammalian stem cells or pluripotent cells, or cells obtained from the recipient mammal which are transformed with DNA encoding a chimeric polypeptide of the invention, e.g., kidney cells.

The general methods for constructing recombinant DNA which can transform target cells are well known to those skilled in the art, and the same compositions and methods of construction may be utilized to produce the DNA useful herein. For example, J. Sambrook et al., *Molecular Cloning: A Laboratory Manual*, Cold Spring Harbor Laboratory Press (2d ed., 1989), provides suitable methods of construction.

The recombinant DNA can be readily introduced into the host cells, e.g., mammalian, bacterial, yeast or insect cells, by transfection with an expression vector comprising DNA encoding a polypeptide by any procedure useful for the introduction into a particular cell, e.g., physical or biological methods, to yield a transformed cell having the recombinant DNA stably integrated into its genome, so that the DNA molecules, sequences, or segments, of the present invention are expressed by the host cell. Preferably, the DNA is introduced into host cells via a vector. The host cell is preferably of eukaryotic origin, e.g., plant, mammalian, insect, yeast or fungal sources, but host cells of non-eukaryotic origin may also be employed.

Physical methods to introduce a recombinant DNA into a host cell include calcium phosphate precipitation, lipofection, particle bombardment, microinjection, electroporation, and the like. Biological methods to introduce the DNA of interest into a host cell include the use of DNA and RNA viral vectors. The main advantage of physical methods is that they are not associated with pathological or oncogenic processes of viruses. However, they are less precise, often resulting in multiple copy insertions, random integration, disruption of foreign and endogenous gene sequences, and unpredictable expression. For mammalian gene therapy, it is desirable to use an efficient means of precisely inserting a single copy gene into the host genome. Viral vectors, and especially retroviral vectors, have become the most widely used method for inserting genes into mammalian, e.g., human cells. Other viral vectors can be derived from poxviruses, herpes simplex virus I, adenoviruses and adeno-associated viruses, and the like. See, for example, U.S. Pat. Nos. 5,350,674 and 5,585,362. Such vectors may be employed to introduce a recombinant DNA encoding a chimeric polypeptide of the invention into a mammal or to a cell intended for implantation into a mammal.

To confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

To detect and quantitate RNA produced from introduced preselected DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the recombinant DNA segment in question, they do not provide information as to whether the preselected DNA segment is being expressed. Expression may be evaluated by specifically identifying the products of the introduced recombinant DNA sequences or evaluating the phenotypic changes brought about by the expression of the introduced recombinant DNA segment in the host cell, e.g., in in vitro or in vivo antiangiogenic, attachment, proliferation and/or migration assays.

B. Synthetic Production of the Chimeric Polypeptide of the Invention

The present isolated, purified peptides, polypeptides, e.g., chimeric polypeptides, which includes variants thereof (i.e., peptides or polypeptides that are substantially similar but not identical in sequence to a reference native peptide or polypeptide), can be synthesized in vitro, e.g., by the solid phase peptide synthetic method or by recombinant DNA approaches (see above). The solid phase peptide synthetic method is an established and widely used method, which is described in the following references: Stewart et al., Solid Phase Peptide Synthesis, W. H. Freeman Co., San Francisco (1969); Merrifield, J. Am. Chem. Soc., 85 2149 (1963); Meienhofer in "Hormonal Proteins and Peptides," ed.; C.H. Li, Vol. 2 (Academic Press, 1973), pp. 48–267; and Bavaay and Merrifield, "The Peptides," eds. E. Gross and F. Meienhofer, Vol. 2 (Academic Press, 1980) pp. 3–285. These peptides or polypeptides can be further purified by fractionation on immunoaffinity or ion-exchange columns; ethanol precipitation; reverse phase HPLC; chromatography on silica or on an anion-exchange resin such as DEAE; chromatofocusing; SDS-PAGE; ammonium sulfate precipitation; gel filtration using, for example, Sephadex G-75; or ligand affinity chromatography.

Once isolated and characterized, derivatives, e.g., chemically derived derivatives, of a given peptide or polypeptide can be readily prepared. For example, amides of the peptide, polypeptide or variants of the present invention may also be prepared by techniques well known in the art for converting a carboxylic acid group At or precursor to an amide. A preferred method for amide formation at the C-terminal carboxyl group is to cleave the peptide or polypeptide from a solid support with an appropriate amine, or to cleave in the presence of an alcohol, yielding an ester, followed by aminolysis with the desired amine.

Salts of carboxyl groups of a peptide, polypeptide or variant of the invention may be prepared in the usual manner by contacting the peptide or polypeptide with one or more equivalents of a desired base such as, for example, a metallic hydroxide base, e.g., sodium hydroxide; a metal carbonate or bicarbonate base such as, for example, sodium carbonate or sodium bicarbonate; or an amine base such as, for example, triethylamine, triethanolamine, and the like.

N-acyl derivatives of an amino group of the peptide, polypeptide or variant may be prepared by utilizing an N-acyl protected amino acid for the final condensation, or by acylating a protected or unprotected peptide. O-acyl derivatives may be prepared, for example, by acylation of a free hydroxy peptide or peptide resin. Either acylation may be carried out using standard acylating reagents such as acyl halides, anhydrides, acyl imidazoles, and the like. Both N- and O-acylation may be carried out together, if desired.

Formyl-methionine, pyroglutamine and trimethyl-alanine may be substituted at the N-terminal residue of the peptide or peptide variant. Other amino-terminal modifications include aminooxypentane modifications (see Simmons et al. 1997)).

The two individual moieties, whether produced synthetically or recombinantly, may be chemically bonded together by any of a variety of well-known chemical procedures. For example, the linkage may be by way of heterobifunctional cross-linkers, e.g., SPDP, carbodiimide, glutaraldehyde, or the like. Production of various immunotoxins, as well as chemical conjugation methods, are well-known within the art and can be found, for example in Thorpe et al. 1982; Waldmann 1991; Vitetta et al.,1987; Pastan et al. 1986; and Thorpe et al. 1987. These methods generally conjugate the two by means of cross-linking agents that introduce a disulfide bond between the two polypeptides. Other preferred reagents are 2-iminothiolane hydrochloride (2IT), sodium S-4-succinimidyloxycarbonyl—methyl benzyl thiosulfate (SMBT) and 2IT or succinimidyloxy carbonyl—methyl- (2-pyridyldithio)-toluene and 2IT. Each group of reagents introduces a disulfide bond between the two moieties which is reducible, but the bond is also resistant to breakdown providing stability of the chimera in vitro and in vivo. Upon internalization into lysosomes or endosomes by the target cell, the bond is reduced.

In addition, the amino acid sequence of a peptide or polypeptide can be modified so as to result in a peptide or polypeptide variant. The modification includes the substitution of at least one amino acid residue in the peptide for another amino acid residue, including substitutions which utilize the D rather than L form, as well as other well known amino acid analogs. These analogs include phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3- carboxylic acid, penicillamine, ornithine, citruline, α-methyl-alanine, para-benzoyl-phenylalanine, phenylglycine, propargylglycine, sarcosine, and tert-butylglycine.

Figure 10:
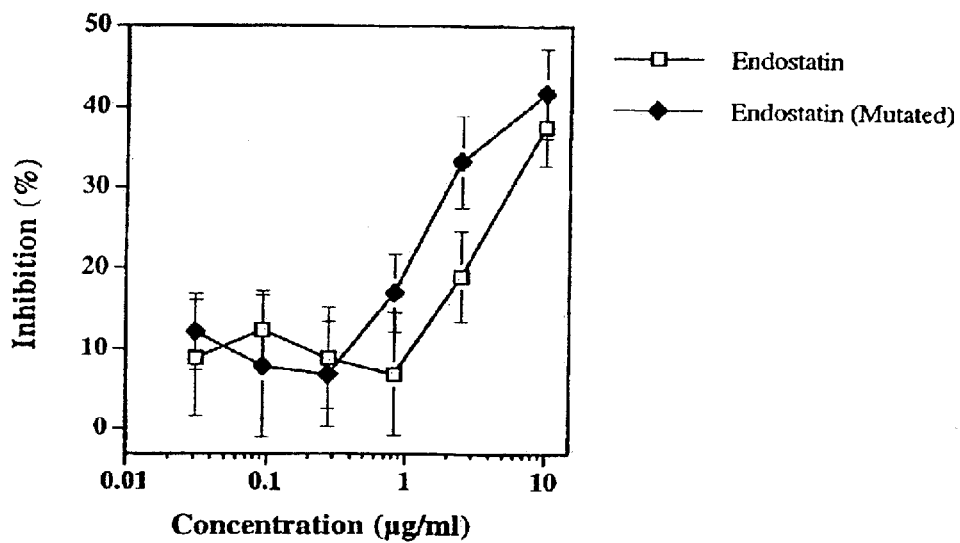
FIG. 10. A Comparison of the Inhibition of Proliferation by Endostatin and Mutated (Variant) Endostatin. The mutated endostatin has an alanine rather than a proline at residue 125. The mutant endostatin (IC30=2.17 micrograms/ml) inhibited BCE proliferation 3.2 times better than native endostatin (IC30+6.95 micrograms/ml).

One or more of the residues of the peptide or polypeptide can be altered, so long as the peptide or polypeptide variant is biologically active. For example, it is preferred that the variant has at least about 10% of the biological activity of the corresponding non-variant peptide or polypeptide. Conservative amino acid substitutions are preferred—that is, for example, aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids. After the substitutions are introduced, the variants are screened for biological activity. Preferred substitutions are those in close proximity to residue 125 (proline), including residues 115 to 135. It was found that substituting alanine for proline at position 125 of endostatin improved biological activity by 3-fold (FIG. 10). Hence, other substitutions in this region may alter, preferably enhance, the activity of endostatin. For example, hydrophobic residues other than alanine at position 125 may also result in improved biological activity.

Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gin, his, lys, arg;
(5) residues that influence chain orientation: gly, pro; and
(6) aromatic; trp, tyr, phe.

The invention also envisions peptide or polypeptide variants with non-conservative substitutions. Non-conservative substitutions entail exchanging a member of one of the classes described above for another.

Acid addition'salts of the peptide, polypeptide or variant thereof, or of amino residues of the peptide, polypeptide or variant thereof, may be prepared by contacting the peptide, polypeptide or amine with one or more equivalents of the desired inorganic or organic acid, such as, for example, hydrochloric acid. Esters of carboxyl groups of the peptides or polypeptides may also be prepared by any of the usual methods known in the art.

II. Dosages, Formulations and Routes of Administration of the Chimeric Polypeptides. Recombinant Polynucleotides and Transformed Cells of the Invention The chimeric polypeptides of the invention and recombinant polynucleotides which encode a chimeric polypeptide of the invention, including their salts, and host cells transformed with the recombinant polynucleotide, are preferably administered in an antiangiogenic amount. To achieve this effect(s), the polypeptide or polynucleotide, or a variant thereof, or a combination thereof, may be administered at dosages of at least about 0.001 to about 100 mg/kg, more preferably about 0.01 to about 10 mg/kg, and even more preferably about 0.1 to about 5 mg/kg, of body weight, although other dosages may provide beneficial results. The transformed host cell may be administered at dosages of at least about $10^3$ cells to about $10^{12}$ cells or more, more preferably about $10^4$ cells to about $10^{11}$ cells, and even more preferably about $10^5$ cells to about $10^{10}$ cells, although other dosages may provide beneficial results. The polynucleotide may be administered as DNA or via a delivery vehicle such as a recombinant virus, recombinant host cell or liposome. The amount administered will vary depending on various factors including, but not limited to, the agent(s) chosen, the weight, the physical condition, and the age of the mammal, and whether prevention or treatment is to be achieved. Such factors can be readily determined by the clinician employing animal models or other test systems which are well known to the art.

Administration of the therapeutic agents in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated.

To prepare the composition, polypeptides are produced recombinantly or otherwise obtained, e.g., synthesized, then purified, lyophilized and stabilized. The polypeptide can then be adjusted to the appropriate concentration, and optionally combined with other agents. For example, an antiangiogenic polypeptide having a targeting moiety specific for endothelial cells may be administered alone, with other antiangiogenic agents, and/or in combination with traditional chemotherapy and/or radiotherapy agents.

Thus, one or more suitable unit dosage forms comprising the therapeutic agents of the invention, which, as discussed below, may optionally be formulated for sustained release. For example, the unit dosage forms of the invention may be formulated using microencapsulation, see WO 94/07529, and U.S. Pat. No. 4,962,091 the disclosures of which are incorporated by reference herein. Materials for microencapsulation include, for example, polymer capsules, alginate-poly-L-lysine-alginate microcapsules, barium poly-L-lysine alginate capsules, barium alginate capsules, polyacrylonitrile/polyvinylchloride (PAN/PVC) hollow fibers, and polyethersulfone (PES) hollow fibers. Preferred carriers are polysaccharides such as hyaluronic acid, sodium alginate and dextran sulfate. More preferably, a therapeutic agent of the invention is encapsulated in alginate beads. See, for example, U.S. Pat. No. 5,879,712.

Alginates also have been used in fluid suspensions for many years because of their ability to form a gel upon contact with gastric fluids. Alginate is a collective term for a family of copolymers containing 1,4-linked β-D-mannuronic and α-L-guluronic acid residues in varying proportions and sequential arrangement. Alginate forms gels with divalent ions like calcium, and the gel-forming properties are strongly correlated with the proportion and lengths of the blocks of contiguous L-guluronic acid residues in the polymeric chains (Martinsen et al., 1989). Preferred sustained release dosage forms comprise a therapeutic agent of the invention, e.g., a chimeric polypeptide or transformed host cell, encapsulated in alginate beads (see, for example, Read et al., 2001; Joki et al., 2001).

Thus, the unit dosage forms comprising the therapeutic agents of the invention can be administered by a variety of routes including oral, or parenteral, including by rectal, transdermal, subcutaneous, intravenous, intramuscular, intraperitoneal, intrathoracic, intrapulmonary and intranasal (respiratory) routes. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for oral administration, they are preferably combined with a pharmaceutically acceptable carrier, diluent or excipient to form a pharmaceutical formulation, or unit dosage form. Preferably, orally administered therapeutic agents of the invention are formulated for sustained release, e.g., the agents are microencapsulated. The total active ingredients in such formulations comprise from 0.1 to 99.9% by weight of the formulation. By "pharmaceutically acceptable" it is meant the carrier, diluent, excipient, and/or salt must be compatible with the other ingredients of the formulation, and not deleterious to the recipient thereof. The active ingredient for oral administration may be present as a powder or as granules; as a solution, a suspension or an emulsion; or in achievable base such as a synthetic resin for ingestion of the active ingredients from a chewing gum. The active ingredient may also be presented as a bolus, electuary or paste.

Pharmaceutical formulations containing the therapeutic agents of the invention can be prepared by procedures known in the art using well-known and readily available ingredients. For example, the agent can be formulated with common excipients, diluents, or carriers, and formed into tablets, capsules, suspensions, powders, and the like. Examples of excipients, diluents, and carriers that are suitable for such formulations include the following fillers and extenders such as starch, sugars, mannitol, and silicic derivatives; binding agents such as carboxymethyl cellulose, HPMC and other cellulose derivatives, alginates, gelatin, and polyvinyl-pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

For example, tablets or caplets containing the agents of the invention can include buffering agents such as calcium carbonate, magnesium oxide and magnesium carbonate. Caplets and tablets can also include inactive ingredients such as cellulose, pregelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, and zinc stearate, and the like. Hard or soft gelatin capsules containing an agent of the invention can contain inactive ingredients such as gelatin, microcrystalline cellulose, sodium lauryl sulfate, starch, talc, and titanium dioxide, and the like, as well as liquid vehicles such as polyethylene glycols (PEGs) and vegetable oil. Moreover, enteric coated caplets or tablets of an agent of the invention are designed to resist disintegration in the stomach and dissolve in the more neutral to alkaline environment of the duodenum.

The therapeutic agents of the invention can also be formulated as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable vehicles and adjuvants which are well known in the art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol", polyglycols and polyethylene glycols, C1–C4 alkyl esters of short-chain acids, preferably ethyl or isopropyl lactate, fatty acid triglycerides such as the products marketed under the name "Miglyol", isopropyl myristate, animal, mineral and vegetable oils and polysiloxanes.

The compositions according to the invention can also contain thickening agents such as cellulose and/or cellulose derivatives. They can also contain gums such as xanthan, guar or carbo gum or gum arabic, or alternatively polyethylene glycols, bentones and montmorillonites, and the like.

It is possible to add, if necessary, an adjuvant chosen from antioxidants, surfactants, other preservatives, film-forming, keratolytic or comedolytic agents, perfumes and colorings. Also, other active ingredients may be added, whether for the conditions described or some other condition.

For example, among antioxidants, t-butylhydroquinone, butylated hydroxyanisole, butylated hydroxytoluene and alpha-tocopherol and its derivatives may be mentioned. The galenical forms chiefly conditioned for topical application take the form of creams, milks, gels, dispersion or microemulsions, lotions thickened to a greater or lesser extent, impregnated pads, ointments or sticks, or alternatively the form of aerosol formulations in spray or foam form or alternatively in the form of a cake of soap.

Additionally, the agents are well suited to formulation as sustained release dosage forms and the like. The formulations can be so constituted that they release the active ingredient only or preferably in a particular part of the intestinal or respiratory tract, possibly over a period of time. The coatings, envelopes, and protective matrices may be made, for example, from polymeric substances, such as polylactide-glycolates, liposomes, microemulsions, microparticles, nanoparticles or waxes. These coatings, envelopes, and protective matrices are useful to coat indwelling devices, e.g., stents, catheters, peritoneal dialysis tubing, and the like. Preferably, the peptides are formulated as microspheres or nanospheres.

The therapeutic agents of the invention can be delivered via patches for transdermal administration. See U.S. Pat. No. 5,560,922 for examples of patches suitable for transdermal delivery of a therapeutic agent. Patches for transdermal delivery can comprise a backing layer and a polymer matrix which has dispersed or dissolved therein a therapeutic agent, along with one or more skin permeation enhancers. The backing layer can be made of any suitable material which is impermeable to the therapeutic agent. The backing layer serves as a protective cover for the matrix layer and provides also a support function. The backing can be formed so that it is essentially the same size layer as the polymer matrix or it can be of larger dimension so that it can extend beyond the side of the polymer matrix or overlay the side or sides of the polymer matrix and then can extend outwardly in a manner that the surface of the extension of the backing layer can be the base for an adhesive means. Alternatively, the polymer matrix can contain, or be formulated of, an adhesive polymer, such as polyacrylate or acrylate/vinyl acetate copolymer. For long-term applications it might be desirable to use microporous and/or breathable backing laminates, so hydration or maceration of the skin can be minimized.

Examples of materials suitable for making the backing layer are films of high and low density polyethylene, polypropylene, polyurethane, polyvinylchloride, polyesters such as poly(ethylene phthalate), metal foils, metal foil laminates of such suitable polymer films, and the like. Preferably, the materials used for the backing layer are laminates of such polymer films with a metal foil such as aluminum foil. In such laminates, a polymer film of the laminate will usually be in contact with the adhesive polymer matrix.

The backing layer can be any appropriate thickness which will provide the desired protective and support functions. A suitable thickness will be from about 10 to about 200 microns.

Generally, those polymers used to form the biologically acceptable adhesive polymer layer are those capable of forming shaped bodies, thin walls or coatings through which therapeutic agents can pass at a controlled rate. Suitable polymers are biologically and pharmaceutically compatible, nonallergenic and insoluble in and compatible with body fluids or tissues with which the device is contacted. The use of soluble polymers is to be avoided since dissolution or erosion of the matrix by skin moisture would affect the release rate of the therapeutic agents as well as the capability of the dosage unit to remain in place for convenience of removal.

Exemplary materials for fabricating the adhesive polymer layer include polyethylene, polypropylene, polyurethane, ethylene/propylene copolymers, ethylene/ethylacrylate copolymers, ethylene/vinyl acetate copolymers, silicone elastomers, especially the medical-grade polydimethylsiloxanes, neoprene rubber, polyisobutylene, polyacrylates, chlorinated polyethylene, polyvinyl chloride, vinyl chloride-vinyl acetate copolymer, crosslinked polymethacrylate polymers (hydrogel), polyvinylidene chloride, poly(ethylene terephthalate), butyl rubber, epichlorohydrin rubbers, ethylenvinyl alcohol copolymers, ethylene-vinyloxyethanol copolymers; silicone copolymers, for example, polysiloxane-polycarbonate copolymers, polysiloxanepolyethylene oxide copolymers, polysiloxane-polymethacrylate copolymers, polysiloxane-alkylene copolymers (e.g., polysiloxane-ethylene copolymers), polysiloxane-alkylenesilane copolymers (e.g., polysiloxane-ethylenesilane copolymers), and the like; cellulose polymers, for example methyl or ethyl cellulose, hydroxy propyl methyl cellulose, and cellulose esters; polycarbonates; polytetrafluoroethylene; and the like.

Preferably, a biologically acceptable adhesive polymer matrix should be selected from polymers with glass transition temperatures below room temperature. The polymer may, but need not necessarily, have a degree of crystallinity at room temperature. Cross-linking monomeric units or sites can be incorporated into such polymers. For example, cross-linking monomers can be incorporated into polyacrylate polymers, which provide sites for cross-linking the matrix after dispersing the therapeutic agent into the polymer. Known cross-linking monomers for polyacrylate polymers include polymethacrylic esters of polyols such as butylene diacrylate and dimethacrylate, trimethylol propane trimethacrylate and the like. Other monomers which provide such sites include allyl acrylate, allyl methacrylate, diallyl maleate and the like.

Preferably, a plasticizer and/or humectant is dispersed within the adhesive polymer matrix. Water-soluble polyols are generally suitable for this purpose. Incorporation of a humectant in the formulation allows the dosage unit to absorb moisture on the surface of skin which in turn helps to reduce skin irritation and to prevent the adhesive polymer layer of the delivery system from failing.

Therapeutic agents released from a transdermal delivery system must be capable of penetrating each layer of skin. In order to increase the rate of permeation of a therapeutic agent, a transdermal drug delivery system must be able in particular to increase the permeability of the outermost layer of skin, the stratum corneum, which provides the most resistance to the penetration of molecules. The fabrication of patches for transdermal delivery of therapeutic agents is well known to the art.

For topical administration, the therapeutic agents may be formulated as is known in the art for direct application to a target area. Conventional forms for this purpose include wound dressings, coated bandages or other polymer coverings, ointmnents, creams, lotions, pastes, jellies, sprays, and aerosols. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredients can also be delivered via iontophoresis, e.g., as disclosed in U.S. Pat. Nos. 4,140,122; 4,383,529; or 4,051,842. The percent by weight of a therapeutic agent of the invention present in a topical formulation will depend on various factors, but generally will be from 0.01% to 95% of the total weight of the formulation, and typically 0.1–25% by weight.

Drops, such as eye drops or nose drops, may be formulated with an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

The therapeutic agent may further be formulated for topical administration in the mouth or throat. For example, the active ingredients may be formulated as a lozenge further comprising a flavored base, usually sucrose and acacia or tragacanth; pastilles comprising the composition in an inert base such as gelatin and glycerin or sucrose and acacia; and mouthwashes comprising the composition of the present invention in a suitable liquid carrier.

The agent may be administered to the respiratory tract. Thus, the present invention also provides aerosol pharmaceutical formulations and dosage forms for use in the methods of the invention. In general, such dosage forms comprise an amount of at least one of the agents of the invention effective to treat or prevent the clinical symptoms of a specific indication or disease. Any statistically significant attenuation of one or more symptoms of an indication or disease that has been treated pursuant to the method of the present invention is considered to be a treatment of such indication or disease within the scope of the invention.

It will be appreciated that the unit content of active ingredient or ingredients contained in an individual aerosol dose of each dosage form need not in itself constitute an effective amount for treating the particular indication or disease since the necessary effective amount can be reached by administration of a plurality of dosage units. Moreover, the effective amount may be achieved using less than the dose in the dosage form, either individually, or in a series of administrations.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions such as phosphate buffered saline solutions pH 7.0–8.0. saline solutions and water.

The agents of the present invention can be administered as a dry powder or in an aqueous solution. Preferred aerosol pharmaceutical formulations may comprise, for example, a physiologically acceptable buffered saline solution. containing between about 0.1 mg/ml and about 100 mg/ml of one or more of the agents of the present invention specific for the indication or disease to be treated.

Dry aerosol in the form of finely divided solid peptide or nucleic acid particles that are not dissolved or suspended in a liquid are also useful in the practice of the present invention. Peptide or nucleic acid may be in the form of dusting powders and comprise finely divided particles having an average particle size of between about 1 and 5 $\mu$m, preferably between 2 and 3 $\mu$m. Finely divided particles may be prepared by pulverization and screen filtration using techniques well known in the art. The particles may be administered by inhaling a predetermined quantity of the finely divided material, which can be in the form of a powder.

For administration to the upper (nasal) or lower respiratory tract by inhalation, the therapeutic agents of the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Nebulizers include, but are not limited to, those described in U.S. Pat. Nos. 4,624,251; 3,703,173; 3,561,444; and 4,635,627.

Alternatively, for administration by inhalation or insufflation, the composition may take the form of a dry powder, for example, a powder mix of the therapeutic agent and a suitable powder base such as lactose or starch. The powder composition may be presented in unit dosage form in, for example, capsules or cartridges, or, e.g., gelatine or blister packs from which the powder may be administered with the aid of an inhalator, insufflator, or a metered-dose inhaler (see, for example, the pressurized metered dose inhaler (MDI) and the dry powder inhaler disclosed in Newman, S. P. in Aerosols and the Lung, Clarke, S. W. and Davia, D. eds., pp. 197–224, Butterworths, London, England, 1984).

Aerosol delivery systems of the type disclosed herein are available from numerous commercial sources including Fisons Corporation (Bedford, Mass.), Schering Corp. (Kenilworth, N.J.) and American Pharmoseal Co., (Valencia, Calif.).

For intra-nasal administration, the therapeutic agent may be administered via nose drops, a liquid spray, such as via a plastic bottle atomizer or metered-dose inhaler. Typical of atomizers are the Mistometer (Wintrop) and the Medihaler (Riker).

The formulations and compositions described herein may also contain other ingredients such as antimicrobial agents, or preservatives. Furthermore, the active ingredients may also be used in combination with other therapeutic agents, for example, bronchodilators.

Preferred delivery systems for a peptide can include coupling the peptide to a carrier or an intact attenuated microbe, such as an inactivated virus or attenuated bacterium, e.g., weakened Salmonella, preparing a multiple antigen peptide, using liposomes or other immunostimulating complexes. Preferably, the delivery system enhances the immunogenicity of the peptide. Preferred carrier proteins include large antigenic proteins such as DTD and TTD, or a fusion protein having a carrier protein of bacterial, e.g., Salmonella flagellin, or viral origin. Viral vectors that may be employed to deliver nucleic acid encoding the peptide include, but are not limited to, retroviral vectors, vaccinia virus vectors, adenovirus vectors or canarypox virus vectors.

III. Indications Amenable to Treatment by the Polypeptides of the Invention

Angiogenesis is the process by which new blood vessels are formed. Under homeostatic conditions, angiogenesis is highly regulated. The endothelium lining a blood vessel is normally quiescent. The vascular endothelial cells that form blood vessels rarely proliferate. In cancer, the switch from a resting state to the angiogenic state occurs when homeostasis is altered by pathological processes, such as tumor growth. Under such conditions, angiogenesis is stimulated by a change in the net balance between pro-and antiangiogenic factors. The angiogenic switch can be triggered by an increase in pro-angiogenic factors, or a decrease in antiangiogenic factors.

In healthy adults, angiogenesis occurs during menstrual cycling, wound healing, fetal development, and numerous pathological processes. Disruption of the angiogenesis cascade may be used in the treatment of cancer, heart disease, several forms of blindness, psoriasis and many chronic inflammatory diseases. Indications amenable to treatment by the polypeptides of the invention include those that are characterized by persistent unregulated angiogenesis, i.e., undesirable endothelial cell proliferation. Such indications include, but are not limited to, cancer, e.g., colon cancer, ovarian cancer, rheumatoid arthritis; atherosclerosis; diabetic retinopathy; macular degeneration; and restenosis.

The invention will be described with reference to the following non-limiting example.

EXAMPLE 1

Materials and Methods

Cells and Animals. Bovine adrenal gland capillary endothelial cells (BCE) were obtained from Clonetics Inc. (San Diego, Calif.). Human umbilical vein endothelial cells (HUVEC), passage 2, were kindly provided by Dr. Vercelotti, University of Minnesota. Human colon carcinoma cells, LS 174T, were obtained from American Type Culture Collection (ATCC Number CL-188; American Type Culture Collection, Manassas, Va. 20110–2209). MA148, a human epithelial ovarian carcinoma cell line, was established from a patient with stage III epithelial ovarian cystadenocarcinoma (Ramakrishnan et al. 1996). The human primary melanoma cell line WM35, which expresses $\alpha_v\beta_3$ integrin, was kindly provided by Dr. Joji Iida and Dr. James B. McCarthy (University of Minnesota). Culture conditions for these cell lines have been previously described (Yokoyama et al. 2000). For example, HUVEC were maintained in EGM (Clonetics) supplemented with 10 ng/ml of human epidermal growth factor, 1 µg/ml of hydrocortisone, 12 µg/ml of bovine brain extract, 50 µg/ml of gentamicin sulfate, 50 µg/ml of amphotericin-B, and 5% of fetal bovine serum (FBS). MA148 were maintained in RPMI (GIBCO BRL, Gaithersburg, Md.) supplemented with 10% FBS, 100 unit/ml of penicillin, 100 µg/ml of streptomycin, and 2 mM L-glutamine.

Cloning and Expression of Human Endostatin. The yeast expression system, Pichia pastoris, was purchased from Invitrogen (San Diego, Calif.). Restriction enzymes and Taq DNA polymerase were purchased from Boehringer Mannheim (Indianapolis, Ind.).

The sequence encoding the COOH-terminal portion of human collagen XVIII was amplified by RT-PCR using total RNA (Quick Prep Total RNA Extraction Kit, Amersham Pharmacia biotech, Piscataway, N.J.) isolated from a human term placenta as template. All endostatin constructs that encode an amino or carboxy terminally modified endostatin encode an endostatin with an amino acid substitution at position 125 (proline to alanine).

The following sets of primers were used for amplification.

```
1) human endostatin
5'GGGGAATTCCACAGCCACCGCGACTTCCAG                          (SEQ ID NO:1)
3'GGGGCGGCCGCCTACTTGGAGGCAGTCATGAAGCT                      (SEQ ID NO:2)

2) (His)6-human endostatin
5'GGGGAATTCCATCATCATCATCATCATCACAGCCACCGCGACTTCCAG         (SEQ ID NO:3)
3'GGGGCGGCCGCCTACTTGGAGGCAGTCATGAAGCT                      (SEQ ID NO:2)

3) human endostatin-Myc tag- (His)6
5'GGGGAATTCCACAGCCACCGCGACTTCCAG                          (SEQ ID NO:1)
3'GGGGCGGCCGCCTTGGAGGCAGTCATGAAGCT                         (SEQ ID NO:4)

4) RGD-human endostatin
5'GGGAATTCAGAGGAGATCACAGCCACCGCGACTTCCAG                   (SEQ ID NO:5)
3'GGGGCGGCCGCCTACTTGGAGGCAGTCATGAAGCT                      (SEQ ID NO:2)

5) human endostatin-RGD
5'GGGGAATTCCACAGCCACCGCGACTTCCAG                          (SEQ ID NO:7)
3'GGGGCGGCCGCCTAATCTCCTCTCTTGGAGGCAGTCATGAAGCT             (SEQ ID NO:6)
```

Amplified fragments were purified using a DNA extraction kit (Amicon, Beverly, Mass.), digested with EcoRI and NotI, and cloned into pPICZα-A vector. DNA sequence analysis was carried out by an Applied Biosystems sequencer (ABI 377 at the Advanced Genetic Analysis Center of the University of Minnesota) to verify identity. Plasmid DNA was then linearized at SacI site and used for homologous recombination into the yeast host strain X-33 (Invitrogen) by electroporation. Electroporation was carried out as per manufacturer's protocol (Invitrogen). Recombinant yeast colonies were selected by plating on YPDS plates containing 100 µg/ml and 500 µg/ml of zeocin. Clones that grew well on the YPDS/500 µg/ml zeocin plates were tested and selected for high level expression. Overnight seed cultures grown in presence of 100 µg/ml zeocin were used to inoculate 500 ml of buffered blycerol-complex medium (BMGY) (Invitrogen) in 2-liter baffled flasks. Cells were grown at 250 rpm at 30° C. for 2 days. Subsequently cells were centrifuged at 3000 rpm for 5 minutes, and resuspended in four 2-liter flasks with 500 ml of buffered methanol-complex induction medium (BMMY). After 5 days of culture at 30° C., the supernatants containing the secreted recombinant proteins were harvested.

Purification of Recombinant Proteins. Pichia clones were cultured in baffled shaker flasks and induced by methanol as previously described (Yokoyama et al. 2000). For large-scale preparations a fermentation procedure was used. A mouse angiostatin expressing Pichia clone (kindly provided by Dr. V. P. Sukhatme) was cultured under similar conditions. Endostatin and angiostatin were purified following published methods (Yokoyama et al. 2000). Culture supernatants were precipitated with 50% saturated ammonium sulfate. Precipitates were dissolved in 10 mM tris-HCl (pH 7.6), 0.5 mM phenylmethylsulfonylfluoride (PMSF) and dialyzed against the same buffer. The concentrated proteins were loaded onto a heparin ceramic (Sigma, Milwaukee, Wis.) column after dialysis against 10 mM Tris-HCl buffer (pH 7.6) containing 0.5 mM PMSF. After thorough washings to remove unbound proteins, endostatin preparations were eluted by a continuous gradient of 0–1 M NaCl in 10 mM Tris-HCl (pH 7.6) buffer. Purified endostatin preparations were analyzed by SDS-PAGE (12% acrylamide gel) under nonreducing conditions and mass spectrometry (data not shown).

Cell Attachment Assay. One nmole/well endostatins or RGD peptide [(H)$_4$-(G)$_3$-R-G-D-(G)$_3$-C] (SEQ ID NO:12), 200 nmol/well vitronectin (GIBCO BRL, Gaithersburg, Md.) or 0.2% gelatin were used to coat 96 well ELISA plates, which do not allow direct cell attachment and spreading. The plates were incubated at 4° C. overnight, and then blocked with 2% BSA in PBS at 37° C. for 2 hours. HUVEC, MA148 (negative control), or WM35 (positive control for $\alpha v\beta 3$ integrin expressing cell line) were harvested by the addition of 1 mM EDTA, and resuspended in EGM medium (HUVEC) or RPMI1640 medium (MA148, WM35). The cells were incubated with or without competitors (1 µg anti-$\alpha v\beta 3$ integrin monoclonal antibody (LM609, Chemicon, Temecula, Calif.) or anti-HLA monoclonal antibody (negative control; G46-2.6, Pharmigen, San Diego, Calif.), or 25 nmole/well RGDS (SEQ ID NO:11) or RGES (SEQ ID NO:10) peptides (Sigma Chemicals, Mo.) for 1 hour at 37° C. Cells were added to the wells at a density of 40,000 cells/well (HUVEC and MA148) or 30,000 cells/well (WM35). After an hour-incubation at 37° C., the plates were washed for 2 times with Hank's balanced salt solution to remove unbound cells. Bound cells were detected by MTT (described later) or Cell Counting Kit-8 (Dojindo, Japan).

The binding of endostatin and RGD-endostatin to HUVEC was assessed by using [$^{125}$I]-labeled proteins. [$^{125}$I]-labeling was carried out by the Iodogen method. HUVEC were harvested by 1 mM EDTA and was resuspended in 0.1% BSA/PBS. Five microliter of [$^{125}$I]-endostatin (27380 cpm/µg) or [$^{125}$I]-RGD-endostatin (32908 cpm/µg) was added to 40,000 cells of HUVEC in 100 µl of 0.1% BSA/PBS. The cells were incubated at room temperature for 1 hour, and then were washed with 0.1% BSA/PBS for 2 times. [$^{125}$I]-endostatin and [$^{125}$I]-RGD-endostatin bound to HUVEC were detected by a gamma-counter (Packard, Meriden, Conn.).

Endothelial Cell Proliferation Assay. The endothelial cell proliferation assay was carried out as described in Yokoyama et al. (2000). Confluent endothelial cells (HUVEC) were trypsinized, and resuspended in M199 (GIBCO BRL) medium with 5% FBS. The cells were then seeded into a gelatinized 96-well culture plate at a density of 5000 cells per well. After 24 hours, different concentrations of endostatin and modified endostatin preparations were added. Twenty minutes later, cultures were treated with 5 ng/ml of basic fibroblast growth factor (bFGF; GIBCO BRL) in the presence of 1 µg/ml heparin. After 72 hours incubation at 37° C., the viability of cells was quantified by the 3-(4,5-dimethylthiazol-2yl)-2,5-dephenyl-2,4-tetrazolium bromide (MTT; Sigma, St. Louis, Mo.) calorimetric assay (Yokoyama et al. 2000).

Endothelial Cell Migration Assay. The migration of HUVEC cells was determined by using Boyden chambers (Neuro Probe, Gaithersburg, Md.). Polycarbonate filters (pore size; 12 µm) were coated with 100 µg/ml collagen type I for overnight at 4° C. HUVEC cells were harvested by 2 mM EDTA in PBS, and the cells (400,000 cells/ml) were added to each well. Six independent experiments were carried out. In two of the experiments, HUVEC were prelabeled with a vital, fluorescence dye, 5 µM 5-(and-6)-carboxyfluorescein diacetate, succinimidyl ester (5(6)-CFDA) (Molecular Probes, Eugene, Oreg.) for 10 minutes at 37° C. Cells were then preincubated with native or RGD-endostatins for 30 minutes at 37° C. Basic FGF (25 µl of 25 ng/ml solution) was added to lower chambers. HUVEC cells (control and treated) were added to upper chambers. After 4 hours of incubation at 37° C., endothelial cells migrated to the bottom side of the membrane were quantified (Ji et al. 1998). Cells remained on the upper side of the membrane were removed by cotton swabs. Migrated cells were fixed by Diff Quick (Baxter, Plymouth, Minn.) and counted using a microscope at 100× magnification. In experiments using CFDA dye, migrated cells were quantified using a fluorescence microscope (Olympus) fitted with FITC filters. The fluorescence images were captured by the Metamorph program and analyzed by Scion Image analysis software (Frederick, Md.).

Tumor Growth Inhibition Studies. Female athymic nude mice (6–8 week-old) were obtained from the National Cancer Institute and allowed to acclimatize to local conditions for one week. Logarithmically growing human colon carcinoma cells (LS174T) and human ovarian carcinoma cells (MA148) were harvested by trypsinization and suspended in fresh medium at a density of $1 \times 10^7$ cells/ml (LS174T) or $2 \times 10^7$ cells/ml (MA148). One hundred µl of the single cell suspension was then subcutaneously injected into the flanks of mice. When the tumors became visible (LS174T; 3 days after inoculation, MA148; 7 days after inoculation), mice were randomized into groups. One group was treated with human endostatin s.c. at a dose of 20 mg/kg/day for 30 days. The second group of mice was treated with RGD-endostatin at the same dose. The third group of mice was treated with endostatin-RGD at the same dose. A control group of mice was treated with sterile PBS under similar conditions. All injections were given subcutaneously near the neck, which is about 2 cm away from the growing tumor mass. Tumor growth was monitored by periodic caliper measurements. Tumor volume was calculated by the following formula. Tumor volume (mm$^3$)=(a× b$^2$)/2 Where in 'a'=length in mm, 'b'=width in mm. Statistical significance between control and treated groups was determined by Repeated measurement analysis of variance. Vessel density and apoptotic index were determined by previously published methods (Wild et al. 2000).

Preparation of Alginate Bead Encapsulated Endostatins and Tumor Growth Inhibition Studies. Alginic acid extracted from Macrocystis pyrifera was purchased from Sigma Chemicals (St. Louis, Mo.). Four percent of alginic acid in water was sterilized by autoclave. Endostatin preparations made in 2% alginic acid were dropped gently into 0.1 M CaCl$_2$ solution using a fine needle under aseptic conditions. The beads were kept at 4° C. overnight and were washed with sterile water before the subcutaneous implantation into tumor bearing mice (MA148 ovarian cancer cell line). Endostatin-encapsulated alginate beads were administered at a dose of 20 mg/kg/mouse/once a week.

Results

To determine whether endostatin could be modified at either of its termini without affecting biological activity, the protein was modified to incorporate a poly-histidine tag on either the amino or carboxyl terminus. Recombinant proteins were purified using a heparin-affinity column, and tested for their ability to inhibit bFGF-induced proliferation of HUVEC cells in vitro. Neither the addition of a His tag at the amino or at the carboxyl terminus of endostatin, nor the addition of a c-Myc tag, affected the ability of endostatin to inhibit BCE cell proliferation or HUVEC migration in vitro when compared to unmodified endostatin preparations (data not shown). Thus, it was determined that human endostatin can be modified at either of its termini without compromising its biological activity. Based on these results, endostatin was modified to incorporate an RGD motif at the amino or carboxyl terminus.

Figure 2A:
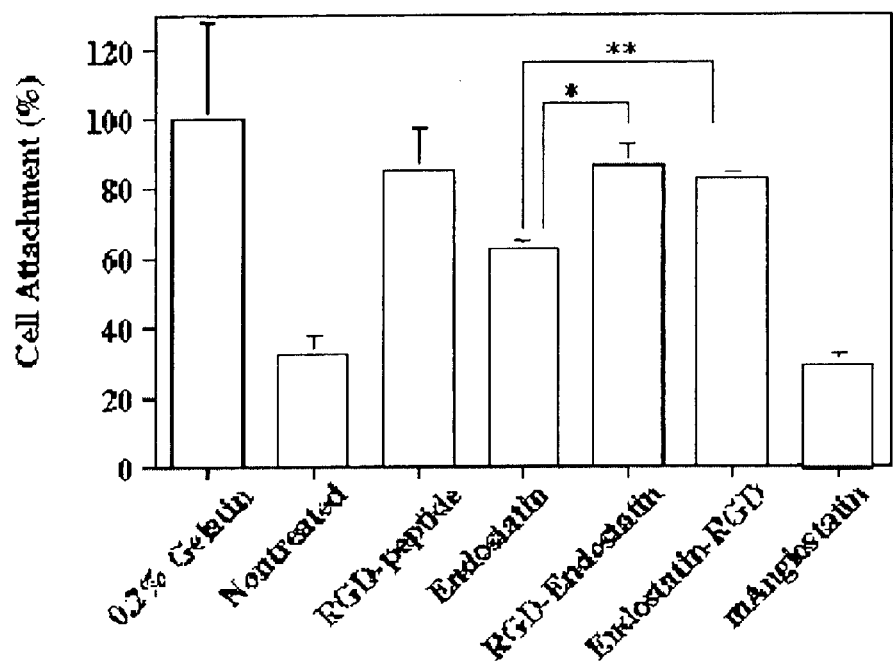
FIG. 2A. Improved Endothelial Cell Attachment to Endostatin by RGD-motif. Human umbilical vein endothelial (HUVEC) cells were added into triplicate wells of ELISA plates coated with endostatins, angiostatin, RGD-peptide at a concentration of 1 nmole/well, or 0.2% gelatin. Bound cells were quantified by MTT method. 100% is equal to the number of cells bound to 0.2% gelatin coated wells. Data are expressed as a mean (columns)±SD (bars). Statistical significance of differences was determined using Student's t-test. *p<0.05.
Figure 2B:
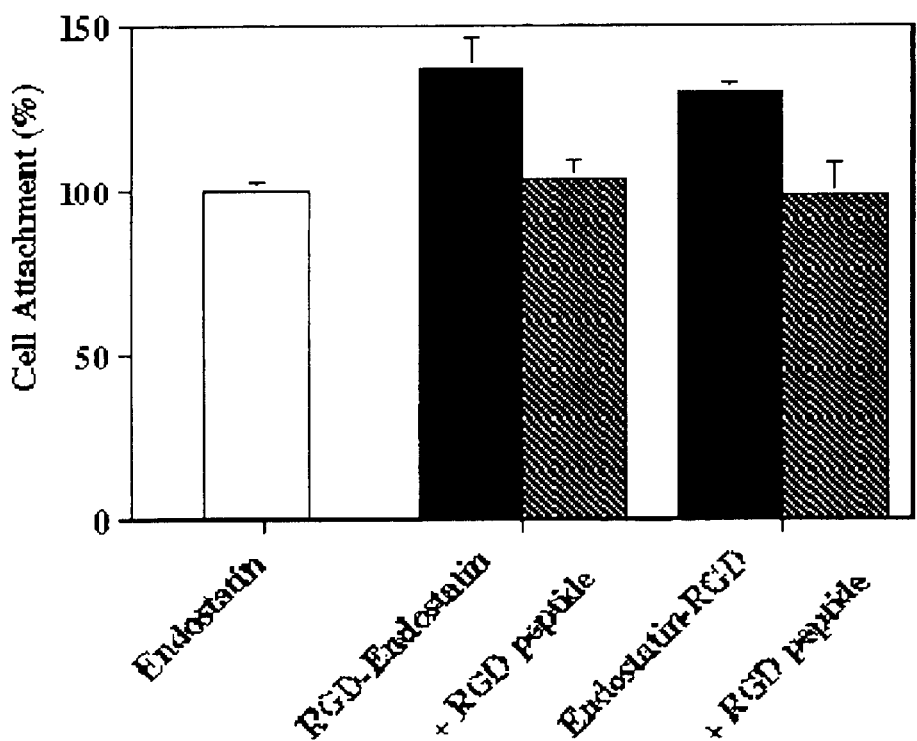
FIG. 2B. Improved Endothelial Cell Attachment to Endostatin by RGD-motif. HUVEC cells were added into triplicate wells of ELISA plates coated with endostatins, angiostatin, RGD-peptide at a concentration of 1 nmole/well, or 0.2% gelatin. Bound cells were quantified by MTT method. Stippled bars show cell attachment in the presence of RGD-peptide (50 nmole/well). 100% is equal to the number of cells bound to endostatin coated wells. Data are expressed as a mean (columns)±SD (bars). Statistical significance of differences was determined using Student's t-test. *p<0.05.

RGD-Endostatin Increases Endothelial Cell Attachment In Vitro. RGD-peptide is well known for its binding to integrins on the surface of endothelial cells. To determine whether the addition of a RGD-motif to endostatin can enhance the binding of endostatin to endothelial cells, cell attachment assays were performed. As a positive control, 0.2% gelatin coated wells were used. HUVEC cells attached to gelatin-coated wells were used as the standard for complete (100%) binding to calculate relative efficiency of endostatin mediated cell attachment (FIG. 2A). BSA blocked wells were used as negative controls. About 30% of HUVEC bound to BSA coated wells. In this assay system, regular (unmodified) endostatin coated wells showed about 60% cell attachment, which was further increased by the RGD-modification (FIG. 2A). RGD-endostatin (p<0.05) and endostatin-RGD (p<0.01) showed about 80% cell attachment. Parallel experiments with RGD-containing synthetic peptide [(H)$_4$-(G)$_3$-R-G-D-(G)$_3$-C] (SEQ ID NO: 12) showed similar binding of HUVEC. Under these experimental conditions, a preparation of recombinant murine angiostatin (kringle 1–4, expressed in yeast) did not result in endothelial cell attachment (FIG. 2A). Cell attachment studies were repeated using human microvascular endothelial cells (MVEC) and bovine adrenal gland capillary endothelial cells (BCE). These studies showed a profile similar to results obtained with HUVEC (data not included).

Figure 2C:
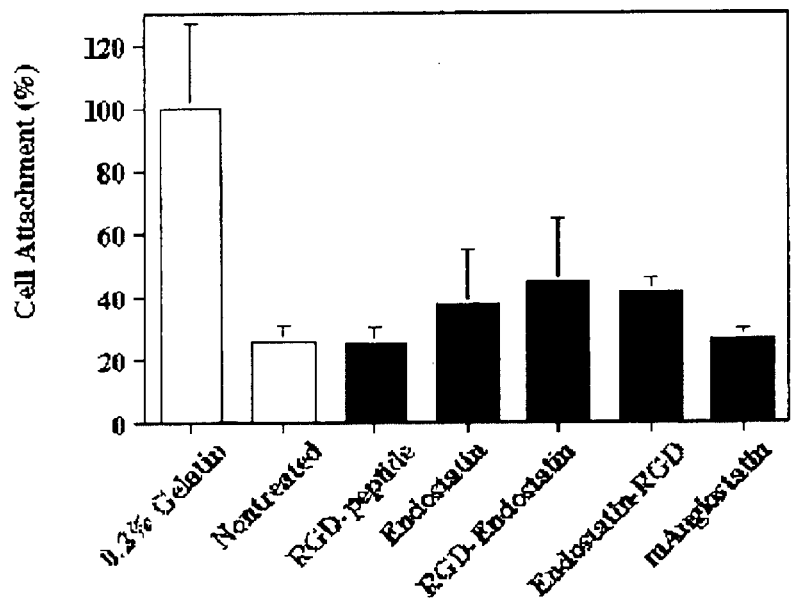
FIG. 2C. Specificity of RGD-Endostatin Mediated Cell Attachment. MA148 cells were added into triplicate wells of ELISA plates coated with endostatins, angiostatin, RGD-peptide at a concentration of 1 nmole/well, or 0.2% gelatin. Bound cells were quantified by MTT method. 100% is equal to the number of cells bound to 0.2% gelatin coated wells. Data are expressed as a mean (columns)±SD (bars). Statistical significance of differences was determined using Student's t-test. *p<0.05.

To determine the specificity of RGD-mediated enhanced binding to endothelial cells, the attachment of RGD endostatin to endothelial cells was compared to that of endostatin. The presence of RGD sequence (COOH or NH2 terminus) increased endothelial cell attachment by 40% over native endostatin. This was completely blocked by RGD containing synthetic peptide. As an additional control, an epithelial ovarian tumor cell line, MA148 was used in cell attachment assays. Results shown in FIG. 2C suggest that RGD-containing peptide did not facilitate MA148 cell attachment. Human endostatin preparations (native and RGD-modified) coated wells again did not show any significant increase in tumor cell attachment when compared to control wells blocked with BSA alone.

Figure 2D:
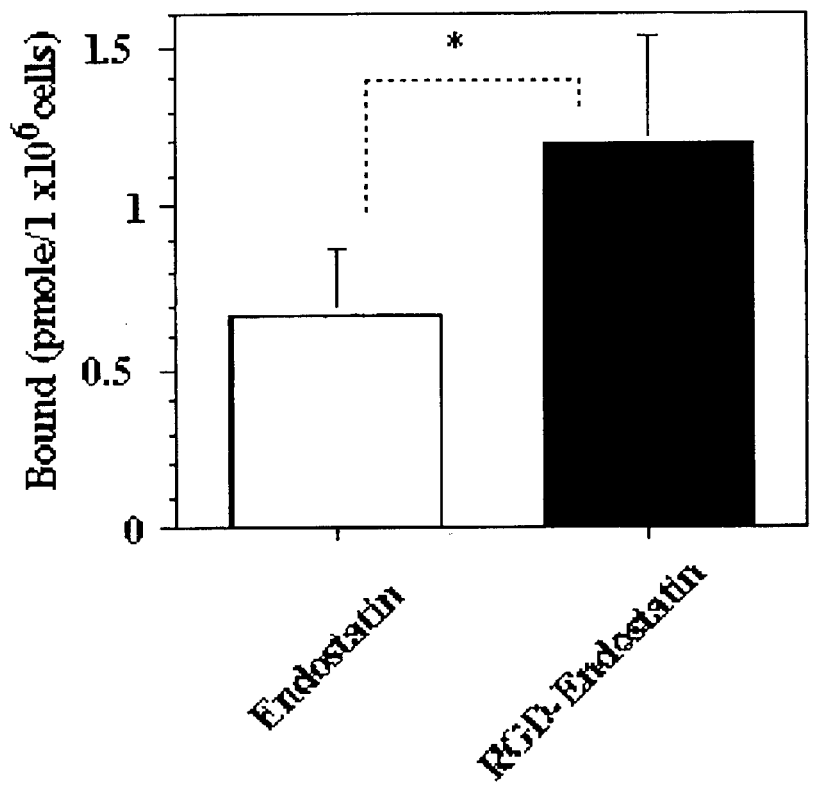
FIG. 2D. Improved Endothelial Cell Attachment by RGD-motif. Direct binding of $[^{125}I]$-endostatin or $[^{125}I]$-RGD-endostatin to HUVEC. Data are expressed as a mean (columns)±SD (bars). Statistical significance of differences was determined using Student's t-test. *p<0.05.

In addition to cell attachment studies, the direct binding of endostatin to HUVEC using [$^{125}$I]-labeled endostatins was examined. Data in FIG. 2D show that about 0.65 pmole of radioiodinated endostatin bound to $10^6$ cells. Under similar conditions, about 1.2 pmole of [$^{125}$I]-RGD-endostatin bound to HUVEC. These studies suggest that endostatin binds endothelial cells and RGD-modification of endostatin increases endothelial cell binding by additional interaction with $\alpha_v\beta_3$ integrin.

Figure 3:
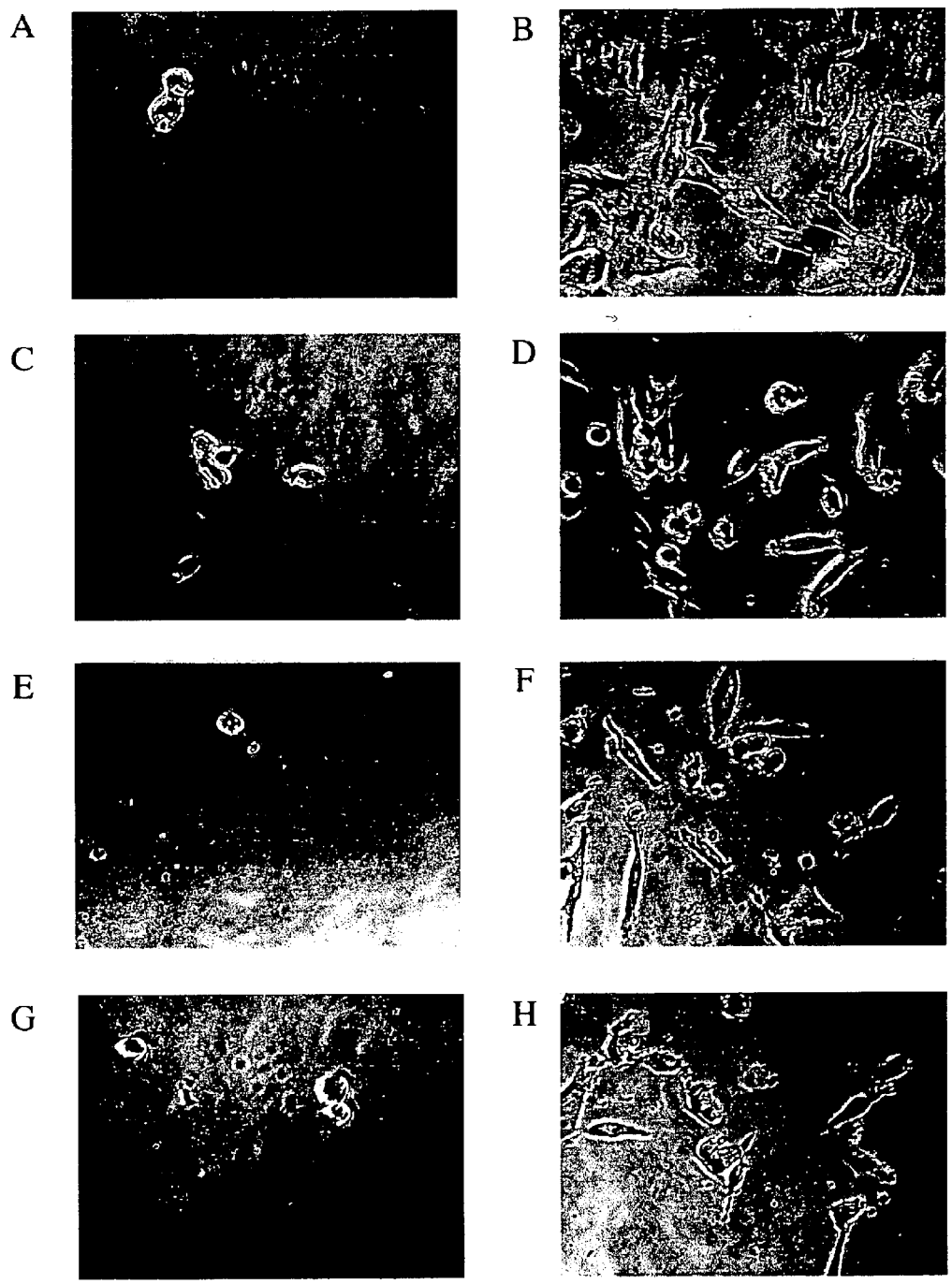
FIG. 3. Specificity of RGD-Endostatin Binding. A human melanoma cell line, WM35, expressing $\alpha v \beta 3$ integrin was used to determine the accessibility and specificity of RGD-endostatin mediated cell attachment. The cell attachment was examined by Olympus BX-60 microscope at 100× magnification. Representative field of attached cells are shown. A, BSA (negative control); B, Vitronectin; C, Endostatin; and D-H, RGD-Endostatin coated wells. Binding of WM35 cells to RGD-endostatin coated wells was completely blocked by preincubation with anti human $\alpha v \beta 3$ antibody (E); anti-HLA antibody (negative control) (F), RGDS (SEQ ID NO:11) peptide (G), or RGES (SEQ ID NO:10) peptide (negative control) (H).
Figure 4:
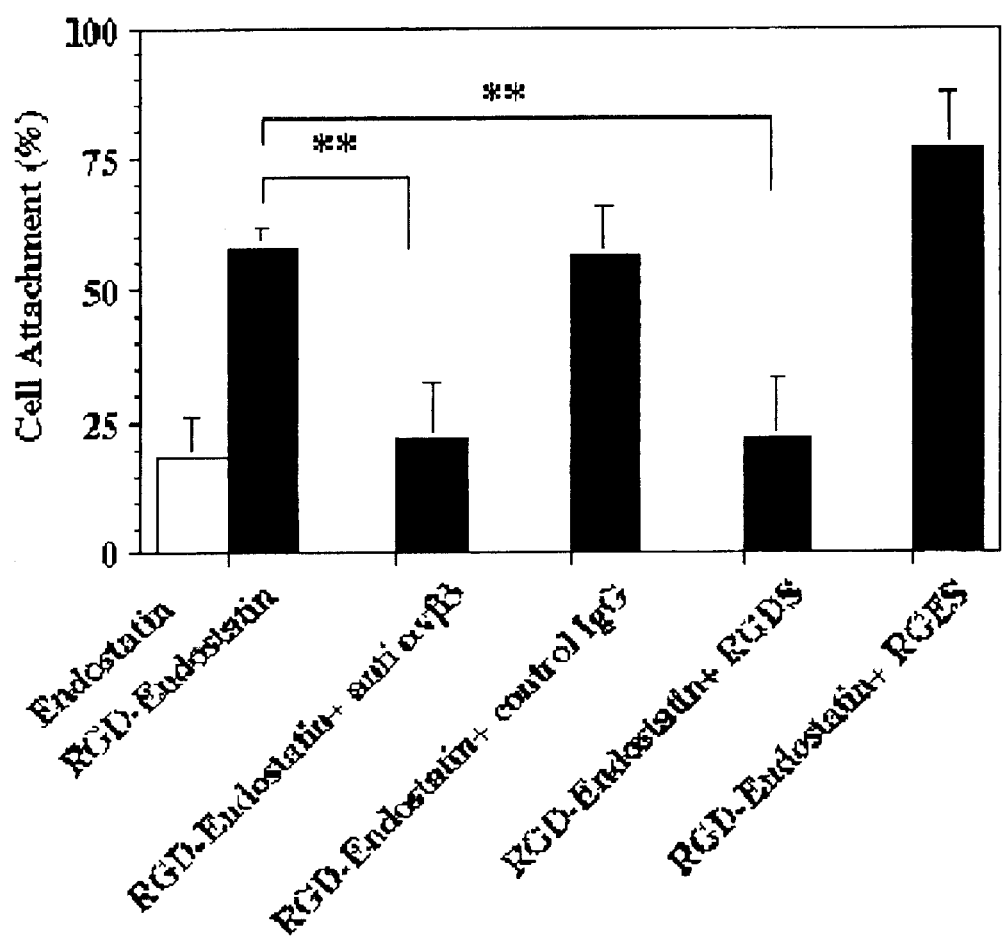
FIG. 4. Binding of Integrin Positive Cells to Endostatin Coated Wells. The number of $\alpha v \beta 3$ positive cells attached to wells coated with different reagents was quantified by Cell Counting Kit-8 (Dojindo, Japan). Cells attached to 0.2% gelatin coated wells were used as 100% to calculate relative number of cells bound to RGD-endostatin coated wells. Data are expressed as a mean (columns)±SD (bars). Statistical significance of differences was determined using Student's t-test. **p<0.01. RGDS is SEQ ID NO:11 and RGES is SEQ ID NO:10.

The human melanoma cell line MW35, which expresses higher levels of $\alpha v\beta 3$ integrin, was used to confirm whether the binding of the RGD moiety in endostatin is available to specifically interact with $\alpha v\beta 3$ integrin. Representative photomicrographs of cell attachment assays are shown in FIG. 3. Unlike HUVEC, MW35 cells did not bind to endostatin by itself (18%, which is similar to BSA blocked control wells) (FIGS. 3A, 3C, and 4). However, MW35 cells specifically attached to RGD-endostatin coated wells (60%) (FIGS. 3D and 4). In order to determine whether the increased binding of RGD-endostatin was indeed specific, two methods were used. In one experiment, a monoclonal antibody to anti-$\alpha v\beta 3$ integrin was used. As a control, isotype matched mouse IgG was used at a similar concentration. Preincubation of MW35 cells with the anti-$\alpha v\beta 3$ integrin antibody completely blocked cell attachment to RGD-endostatin (FIGS. 3E and 4). In contrast, the control antibody did not prevent MW35 cells from binding to RGD-endostatin coated wells (FIGS. 3F and 4). In a second series of experiment, synthetic peptides were used as competitive inhibitors. Inclusion of RGDS (SEQ ID NO:11) peptide in the medium completely prevented attachment of WM35 cells (FIGS. 3G and 4), whereas a control peptide, RGES (SEQ ID NO:10), did not affect MW35 cells from attaching to RGD-endostatin coated wells (FIGS. 3H and 4).

Inhibition of Endothelial Cell Proliferation. To determine whether the modification of human endostatin affects biological activity, endothelial cell proliferation and migration assays were carried out. To evaluate the antiangiogenic activity of human endostatin and its mutants, HUVEC proliferation assay was used. HUVEC were stimulated with bFGF either in the presence or absence of endostatin preparations. Unmodified endostatin alone inhibited HUVEC cell proliferation by 50% at a concentration of 11.4 µg/ml. The presence of the RGD-motif at either N-or C-terminus of endostatin showed further improvement in the inhibition of endothelial cell proliferation. IC$_{50}$ values for RGD-endostatin and endostatin-RGD were 2.4 µg/ml and 5.6 µg/ml respectively. These studies suggest that modification of human endostatin with a RGD-sequence not only increased endothelial cell attachment but also improved its antiproliferative activity.

Figure 5A:
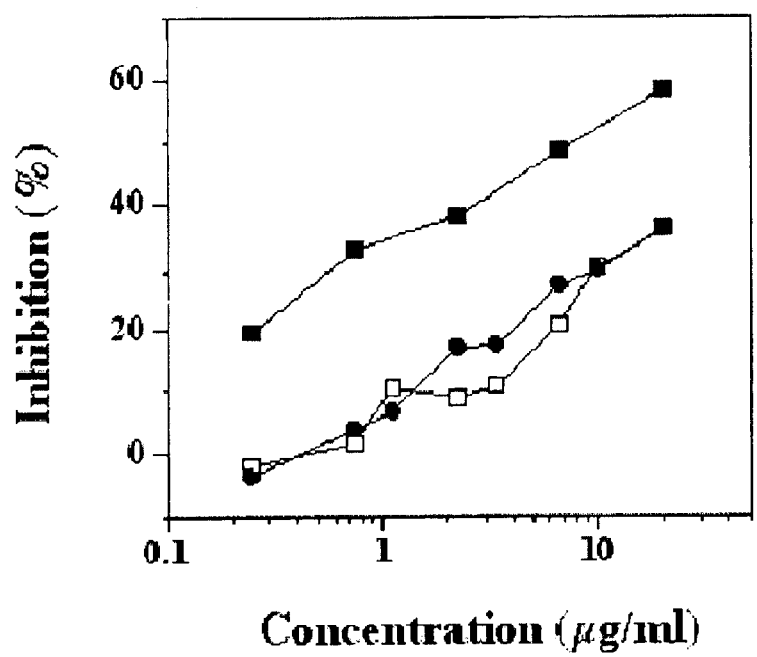
FIG. 5A. Inhibition of Endothelial Cell Proliferation. Purified endostatin or RGD-endostatin was added to bovine adrenal gland capillary endothelial (BCE) cell cultures treated with 5 ng /ml bFGF for 4 days. ●, Endostatin; □, RGD-Endostatin; ■, Endostatin-RGD. Each data point is a mean of triplicate cultures from 5 independent experiments. Each data point of Endostatin-RGD is a mean of triplicate cultures from 4 independent experiments.

Data in FIG. 5A represent the average of 4 (endostatin-RGD) or 5 (endostatin and RGD-endostatin) independent experiments. BCE cell proliferation was inhibited in a concentration dependent manner by the native endostatin. At 20 µg/ml, BCE cell proliferation was inhibited by 30%. Addition of the RGD motif at the amino terminal end of endostatin did not change its inhibitory capacity. In contrast, the RGD modification at the carboxyl terminus of endostatin enhanced its antiproliferative activity by more than 10-fold. For example, a 40% inhibition in BCE proliferation was seen at 1.0 µg/ml of endostatin-RGD construct.

Figure 5B:
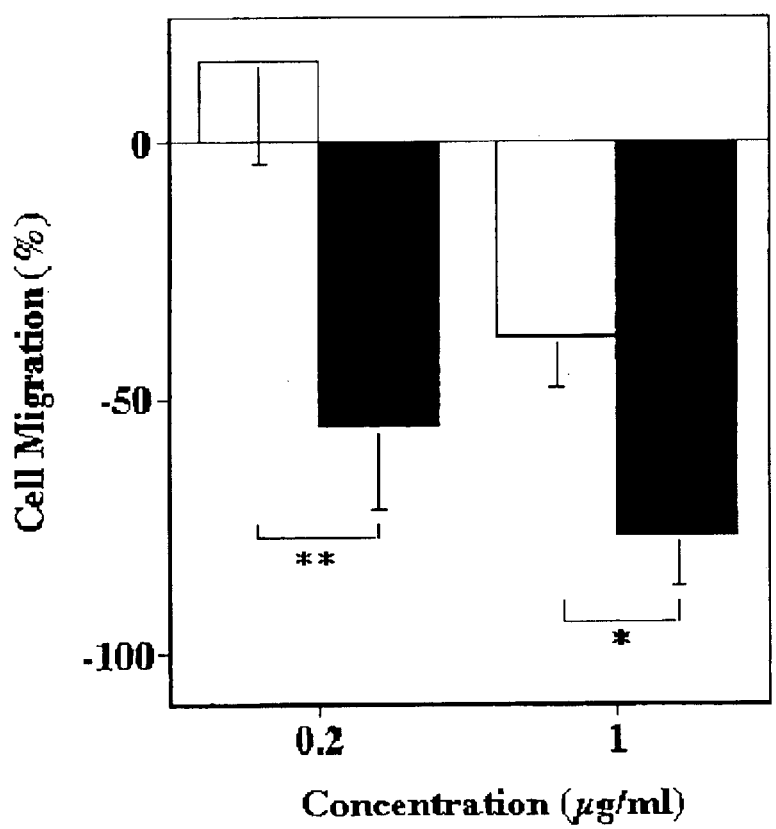
FIG. 5B. Improved Inhibition of Endothelial Migration by RGD-Endostatin. Effect of Endostatin (open bars) and RGD-Endostatin (closed bar) on endothelial cell (HUVEC) migration was determined using Boyden chambers. Basic FGF (25 ng/ml) was used to induce migration of endothelial cells. The '0%' indicates basal level of migration of HUVEC in the presence of bFGF. Negative values represent inhibition of cell migration. Data are expressed as mean (columns) ±SE (bars). Statistical significance was determined using Student's t-test. *p<0.05, **p<0.01.

Increased Inhibition of Endothelial Cell Migration by Endostatin containing RGD-motif. To evaluate whether the RGD-motif can affect the ability of endostatin to inhibit endothelial cell migration, Boyden chamber based migration assays were performed (FIG. 5B). Basic FGF was used as an inducer of endothelial cell migration. Endostatin treatment at 1 µg/ml, for example, inhibited bFGF induced migration by about 42%. At a reduced concentration, 0.2 µg/ml, native endostatin did not inhibit endothelial cell migration. In comparison, RGD-endostatin treatment of HUVEC cells showed a marked improvement in inhibition of cell migration. RGD-endostatin showed more than 55% inhibition even at 0.2 µg/ml concentration, which was statistically significant (p<0.01). A higher concentration (1 µg/ml) of RGD-endostatin showed further improvement in the inhibition of endothelial cell migration (about 80%), which was again statistically significant.

To confirm whether the RGD moiety itself inhibited migration of endothelial cells, CGGGRGD (SEQ ID NO:13) was chemically linked to bovine serum albumin (RGD-BSA) using a heterobifunctional cross-linking reagent, N-succinimidyl 3-[2-pyridyldithio]propionate (SPDP, Pierce Chemicals, Rockford, Ill.). Accessibility of RGD in the BSA conjugate was validated in cell attachment assays (data not shown). Based on molecular weight shift in SDS-PAGE, an average of 5 RGD moieties were introduced per mole of BSA. RGD-BSA did not inhibit migration of HUVEC at equimolar concentration (10–50 nM concentration, data not shown).

These data demonstrate that the modification of endostatin with RGD improves the biological activity of the molecule and increases its ability to inhibit endothelial cell migration and proliferation. In separate experiments (repeated twice), the relative efficiency of inhibiting migration of endothelial cells was compared between amino vs. carboxyl terminal modification of endostatin. These studies showed that at 1 µg/ml concentration endostatin-RGD showed a 60% inhibition of migration whereas, the RGD-endostatin showed about 33% inhibition. Native endostatin showed 20% inhibition at this concentration (data not shown). Although the C-terminal modification had a better effect when compared to the amino terminus addition of RGD sequence, the difference between them was not statistically significant (p=0.1).

Figure 6A:
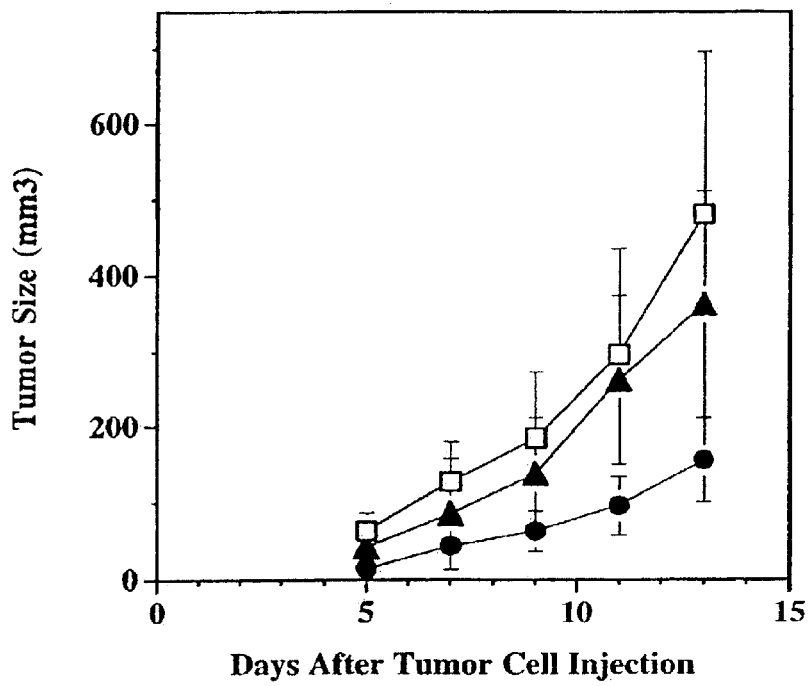
FIG. 6A. Improved Inhibition of Human Colon Cancer by RGD-modified Endostatin. Human colon carcinoma cell line, LS174T was injected s.c. into female athymic mice ($10^6$ cells/mouse). After tumor establishment (3 days) mice were randomized and treated with endostatin, RGD-endostatin and endostatin-RGD (s.c. about 2 cm away from tumor sites) at a dose of 20 mg/kg/day. Treatment was continued for 14 days. □ Endostatin; ● RGD-Endostatin; ▼, Endostatin-RGD. Mean tumor volume of control (LS174T) and treated groups are shown. Statistical significance was determined by Repeated measurement analysis of variance. The error bars indicate SE.

Inhibition of Tumor Growth. To test whether RGD-endostatin could improve anti-tumor activity of endostatin, two xenograft model systems were used. In one of the studies, the human colon carcinoma cell line, LS174T was used. LS174T cells grow very fast, and were first allowed to establish for 3 days. At this time, small palpable tumor nodules could be easily seen by the naked eye. Mice were then randomized and divided into groups. RGD-endostatin and endostatin were administered subcutaneously at a dose of 20 mg/kg/day for a period of 14 days. FIG. 6A shows that RGD-endostatin inhibited tumor growth better than unmodified endostatin, which was statistically significant (p=0.03). In this model system, the control tumors reached a size of about 500 mm$^3$ by day 14. Endostatin treatment inhibited the tumor growth by about 30% under the conditions tested. In contrast, groups of animals treated with RGD-endostatin significantly decreased the tumor growth by 78% when compared to the control animals (p=0.0006).

Figure 6B:
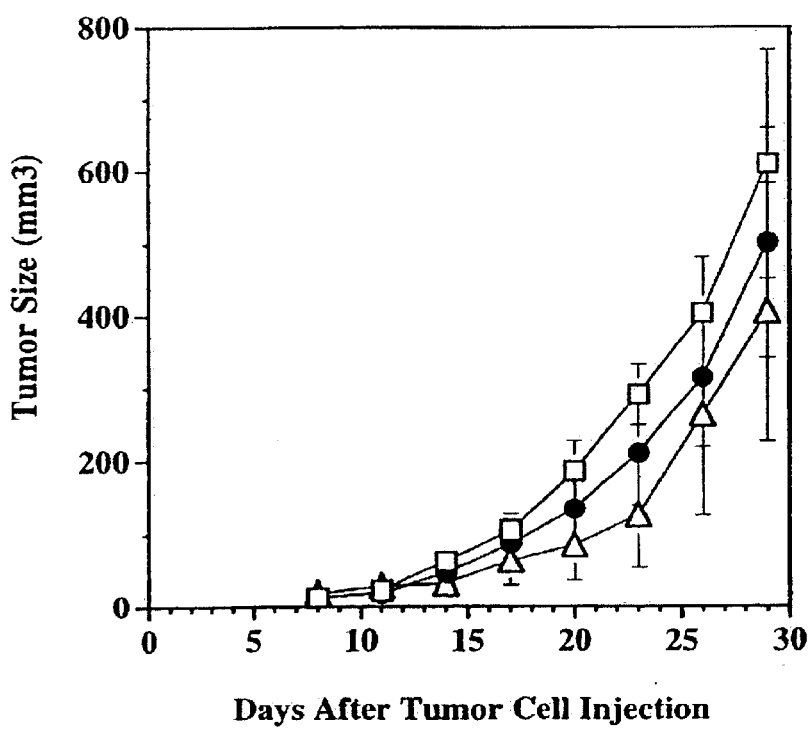
FIG. 6B. Improved Inhibition of Human Ovarian Cancer by RGD-modified Endostatin. Human ovarian carcinoma cell line, MA148 (2×10$^6$ cells) was injected s.c. into female athymic mice. After tumor establishment (7 days), mice were randomized and treated with endostatin, RGD-endostatin and endostatin-RGD (s.c. about 2 cm away from tumor sites) at a dose of 20 mg/kg/day. Treatment was continued for 14 days. □ Endostatin; ● RGD-Endostatin; Δ, Endostatin-RGD. Mean fractional tumor volume (MA148) of control and treated groups are shown. Statistical significance was determined by Repeated measurement analysis of variance. The error bars indicate SE.

The effect of RGD-endostatin in a human ovarian carcinoma model was also tested (FIG. 6B). In this model system, tumor cells were allowed to establish for 7 days before initiating the treatment. Control animals showed an increase of tumor volume by 20-fold when compared to the initial tumor volume before treatment. RGD-endostatin, endostatin-RGD and native endostatin were injected at a dose of 20 mg/kg/day for a total of 21 days. Under these conditions, native endostatin showed no effect when compared to control animals. RGD-endostatin showed a 35% inhibition of tumor growth (about 14 fold increase in initial tumor volume). For comparison, C-terminal modification of endostatin was also used in parallel. Interestingly, endostatin-RGD was found to be more active than RGD-endostatin. Endostatin-RGD, for example, showed a 72% inhibition at a dose of 20 mg/kg/day (FIG. 6B). These animals showed only a 5-fold increase over the initial tumor volume during the treatment period.

Figure 7:
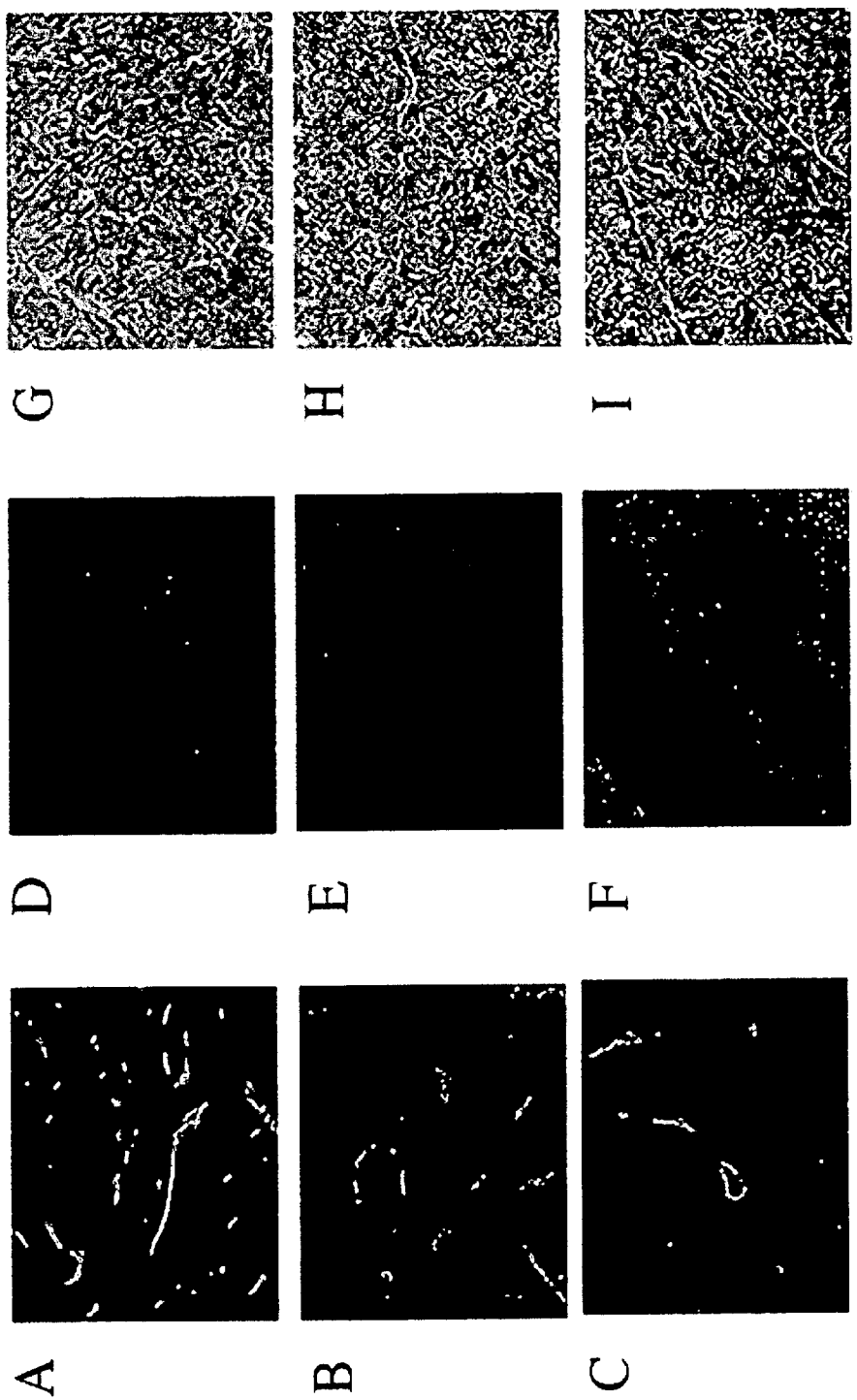
FIG. 7. Histochemical Analysis. Residual tumors from endostatin and RGD-endostatin treated groups were resected 1 day after the completion of treatment. A–C show vessel density as determined by PE labeled anti- CD31 antibody staining; D–F, TUNEL assay; G–I, H&E staining; A, D and G, control; B, E and H; endostatin treated tumor sections; C, F and I; RGD-endostatin treated tumor sections.

Effect on Tumor Blood Vessels and Apoptosis. To evaluate the consequence of antiangiogenic therapy, the residual tumors were examined histologically. Frozen tumor sections were immunohistochemically stained with an endothelial specific antibody against CD31. Both native and RGD-modified endostatin treatment resulted in reduced vessel density (FIGS. 7A–C). The same frozen sections were also analyzed for changes in the viability of tumor cells using a TUNEL assay (FIGS. 7D–F). Serial sections of each tumor were also stained by H & E to assess necrotic changes (FIGS. 7G–I).

Figure 8:
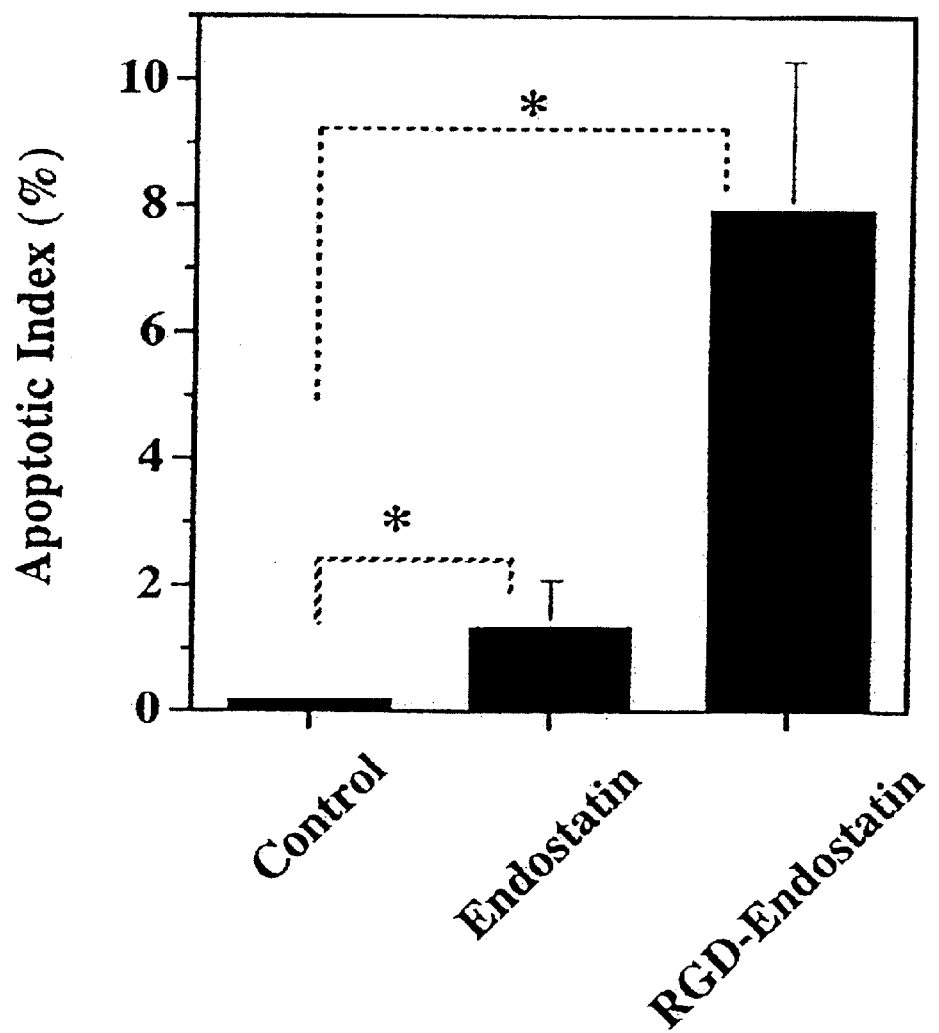
FIG. 8. Apoptotic Cell Analysis. Quantification of apoptotic cells showed a marked increase in RGD-endostatin treated animals. Statistical significance was determined using Student's t-test. *$p<0.05$. The error bars indicate SE.

H & E and TUNEL staining revealed that RGD-endostatin induced more apoptosis in tumor tissue (FIGS. 7F and I) when compared with control (FIGS. 7D and G) and endostatin treated tumors (FIGS. 7E and H). A quantitative analysis of apoptotic index is shown in FIG. 8. RGD-endostatin treated tumors showed an apoptotic index of 7.91±2.40%. This value is about 45-fold higher than the control tumors (0.176±0.048). Native endostatin treated tumors showed an apoptotic index of 1.32±0.774%, an increase of 7.5-fold over the control tumors.

Slow Release of Native Endostatin and Endostatin-RGD by Alginate Beads Improves Anti-tumor Activity. Alginate microspheres were used to investigate whether the slow release of endostatins can further improve the anti-tumor activity. Alginic acid, which is a naturally occurring biopolymer, has been used as a matrix for entrapment and delivery of a variety of biological agents. The ovarian cancer cell line, MA148, was injected s.c. into the flanks of athymic mice. After seven days, alginate beads containing endostatin preparations were implanted into groups of mice. Endostatin was given once a week at a dose of 20 mg/kg. A control group of mice received endostatin free alginate beads once a week.

Figure 9:
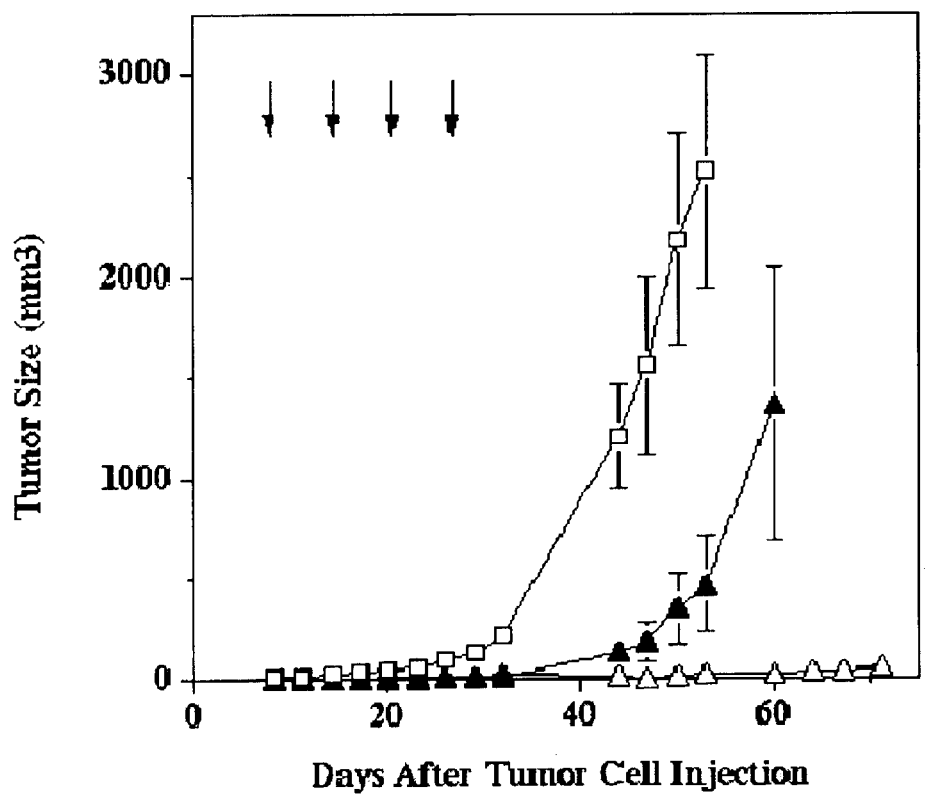
FIG. 9. Complete Inhibition of Ovarian Cancer Growth by Endostatin-RGD Encapsulated into Alginate Beads. Human ovarian carcinoma cell line, MA148, was injected s.c. into female athymic mice. After 7 days to allow tumor establishment, mice were treated with endostatin and endostatin-RGD encapsulated in alginate beads (s.c.) at a dose of 20 mg/kg/week. Treatment was carried out once a week for 4 weeks. □, Alginate bead control; ▼, Endostatin; Δ, Endostatin-RGD. Mean tumor volume of control and treated groups are shown. Statistical significance was determined using Student's t-test. The error bars indicate SE. Arrows show time of treatment.

Native endostatin given in alginate formulation showed a dramatic improvement in anti-tumor activity when compared to the bolus injection schedule (FIGS. 9 and 4, respectively). Bolus administration of native endostatin showed a moderate inhibition on day 20 but did not show any efficacy on subsequent measurements (day 26). In comparison, when native endostatin was administered in an alginate encapsulated bead formulation, there was a significant inhibition of tumor growth. When compared to control animals, alginate endostatin treated group showed more than 80% reduction in tumor volume on day 26 and 87% inhibition on day 32. Even on day 47 (19 days after the last implantation of the beads) the alginate encapsulated endostatin treated animals showed about 80% inhibition when compared to the control animals.

The anti-tumor activity of native endostatin and endostatin-RGD preparations were compared under slow-release conditions against human ovarian cancer. Alginate encapsulated endostatin was subcutaneously implanted into animals once a week at a dose of 20 mg/kg/animal/week. In these experiments, the control tumors reached a size of 2500 mm$^3$ by day 50 and so animals had to be sacrificed. Native endostatin encapsulated into alginate beads showed significant inhibition of tumor growth throughout the experiment. For example, 40% of native endostatin treated animals did not show any tumor growth up to 42 days at which time control animals had a mean tumor volume of 1200 mm$^3$. Subsequently, the tumors began to grow and reached a size of about 1200 mm$^3$ by day 60. Interestingly, endostatin modified with the RGD-motif, when delivered in alginate beads, showed a complete inhibition of tumor growth even at 75 days after tumor cell transplantation (FIG. 14). This data suggest that long-term suppression of tumor growth can be achieved by a slow release formulation of endostatin-RGD construct. Tumor growth was inhibited even after 47 days following the last dose of endostatin-RGD administration.

These studies demonstrate that RGD-modification of endostatin can improve the anti-tumor activity of endostatin and that a slow release formulation can be used to inhibit tumor growth very effectively.

Discussion

Tumor neovascularization is influenced by a balance between a number of positive and negative regulators secreted into the tumor microenvironment. Additionally, interaction between endothelial cell integrins and extra cellular matrix components regulate the angiogenic response. Endothelial cells differentially overexpress $\alpha_v\beta_3/\alpha_v\beta_5$ integrins when treated with growth factors and during vascular remodeling. In contrast, many normal tissues do not show upregulation of $\alpha_v\beta_3/\alpha_v\beta_5$ integrins. Since RGD-containing proteins are one of the targets for $\alpha_v\beta_3/\alpha_v\beta_5$ integrins, it is possible to target therapeutic compounds to vascular endothelial cells by chemically linking them to RGD-peptides (Arap et al., 1998).

Other methods to interfere with integrin-mediated vascular remodeling include the use of cyclic peptides containing RGD, hemopexin domain of metalloproteinases and monoclonal antibodies to specific integrins (Sipkins et al. 1998). Apart from direct interaction with extracellular matrix (ECM), $\alpha_v\beta_3$ integrin also plays a distinct role in vascular remodeling by sequestering MMP-2 in an RGD-independent manner (Brooks et al. 1996). In a recent study, free RGD-peptide has been found to induce apoptosis by direct interaction with caspases inside the cell (Buckley et al. 1999). Thus, RGD-peptide offers not only a method to target therapeutic reagents to tumor vasculature but can also directly influence angiogenic processes.

As described hereinabove, an RGD-motif was added to human endostatin to target the molecule to tumor vasculature so as to improve inhibition of tumor growth. The results showed that endostatin can be modified either at the $NH_2$ or COOH terminus without compromising its biological activity. In contrast to a previous study, modification of endostatin either at the amino or carboxyl terminus by adding poly-histidine residues did not reduce the potency of endostatin to inhibit FGF/VEGF-induced endothelial cell proliferation or its migration (O'Reilly et al. 1997). One possible explanation for this discrepancy could be the inappropriate folding of the bacterially-expressed his tagged endostatin.

Binding to endothelial cells can potentially limit the bioavailability of endostatins when administered systemically. It is interesting to note that even native endostatin showed significant binding to endothelial cells. Angiostatin, another potent antiangiogenic molecule, did not favor endothelial cell attachment. Since endostatin was derived from an ECM component (collagen type XVIII), it may interact with hitherto unidentified cell surface components on the endothelial cells. The primary sequence of endostatin has no RGD motif. However a reverse sequence, DGR, is located at position 104–106 of mouse, but not human, endostatin. DGR does not bind to $\alpha_v\beta_3$ integrin. But mouse and human endostatin have RGAD (SEQ ID NO:14), which is not expected to bind $\alpha_v\beta_3/\alpha_v\beta_5$ integrins. Identifying the cell surface molecule recognizing endostatin is therefore important to understand the mechanism of action of endostatin.

The addition of the RGD-sequence to endostatin significantly improved endothelial cell binding. Moreover, the increased binding was completely blocked by adding a synthetic peptide RGDS (SEQ ID NO:11) or anti-$\alpha v\beta 3$ integrin antibody but not by RGES (SEQ ID NO:10) peptide or a control antibody. Competitive inhibition studies using RGD-peptide did not affect the basal levels of endothelial cell attachment to endostatin-coated plates. These results indicate that RGD-modified endostatins can bind to endothelial cells both via $\alpha_v\beta_3$ integrin and by a second, unknown target molecule. Binding of endostatin to endothelial cells appears to be specific since under similar conditions, endostatin did not bind significantly to an epithelial tumor cell line, which is also used in tumor growth inhibition studies.

Endostatin-RGD, but not RGD-endostatin, showed an increased antiproliferative activity. The RGD-motif also improved the ability of endostatin to inhibit migration of endothelial cells across gelatin-coated membranes. The COOH—terminal addition of RGD resulted in enhanced inhibition of both cell migration and proliferation, whereas the $NH_2$-terminal modification affected only cell migration. Cell attachment and binding studies indicated that RGD was accessible when present at either of the termini.

The increased activity observed with endostatin containing RGD cannot be solely due to the RGD-sequence alone since a chemical conjugate of RGD peptide to BSA did not affect endothelial cell proliferation or inhibit FGF induced cell migration. Therefore, the RGD sequence in the context of endostatin results in the improved antiangiogenic activity. Potential intracellular targets for endostatin include down-regulation of anti-apoptotic protein and activation of caspases (Dhanabal et al. 1999).

The improvement of in vitro endothelial cell binding, and antiproliferative and/or antimigratory activity of the RGD-containing endostatin, likely resulted in the increased anti-tumor activity of RGD-containing endostatins. The growth of human colon carcinoma LS174T was inhibited by RGD-endostatin to a greater extent than by native endostatin. Also, the growth of human ovarian carcinoma MA148 was inhibited by RGD-endostatin to a greater extent than native endostatin. Since endostatin-RGD is capable of inhibiting not only the migration of endothelial cells but also their proliferative response, it may be more active than the RGD-endostatin. Histological analysis indicated that the RGD-motif significantly increased the induction of apoptosis in the tumors by endostatin which may explain the more potent antitumor activity observed with RGD-endostatin administration. It is possible that RGD-endostatin is more potent in activating apoptotic signals by virtue of higher binding to endothelial cells. Alternatively, RGD-endostatin and endostatin-RGD could interfere with a focal adhesion kinase complex, molecular machinery critically involved in cell migration. Growth factor induced signaling is known to crosstalk with integrin-mediated communication with focal adhesion kinase.

The biological half-life and tumor localization of endostatin versus RGD-endostatin was compared. These studies showed a 50% increase in tumor bound RGD-endostatin when compared to native endostatin (data not included). Therefore, the increased anti-tumor activity of RGD-containing endostatin is a result of a) improved biological activity and b) vascular targeting.

The slow release by alginate encapsulation further improves the anti-tumor activity of endostatin and endostatin-RGD revealed that even at a lower dose (1/7), while bolus injections of native endostatin did not show significant inhibition of tumor growth. Further, native endostatin treated animals showed recurrence of the disease upon discontinuation of therapy in this model system. In comparison, endostatin-RGD treatment produced long-term remissions, e.g., tumor growth was completely inhibited for 75 days after tumor cell transplantation. These studies suggest that the RGD-modification is beneficial and that a slow release/infusion of these proteins for prolonged periods would enhance antiangiogenic therapies.

References

Adelman et al., *DNA*, 2, 183 (1983).
Arap, W. et al., *Science*, 279, 377–380 (1998).
Boehm, T. et al., *Nature*, 390, 404–407 (1997).
Brooks, P. C. et al., *J. Clin. Invest.*, 99, 1390–1398 (1997).
Brooks, P. C. et al. *Cell*, 85, 683–693 (1996).
Buckley, C. D. et al., *Nature*, 397, 534–539 (1999).
Carmichael et al., *Cancer Res.*, 47, 936–942 (1987).
Crameri et al., *Nat. Biotech.*, 15 346 (1997).
Crameri et al., *Nature*, 391, 288 (1998).
Crea et al., *Proc. Natl. Acad. Sci. U.S.A.*, 75, 5765 (1978).
Dawson, D. W. et al., *Science*, 28, 245–248 (1999).
Dhanabal, M. et al., *J. Biol. Chem.*, 274, 11721–11726 (1999).
Ferrara, N. et al., *Endocr. Rev.*, 13, 18–32 (1992).
Folkman, J., *Mol Med.*, 1, 120–122 (1995).
Folkman, J., *J. Natl. Cancer Inst.*, 82, 4–6 (1990).
Friedlander, M. et al., *Science*, 270, 1500–1502 (1995).
Goeddel et al., Nucleic Acids Res., 8, 4057 (1980).
Ji et al., *Biochem. Biophys. Res. Commun.*, 247, 414–419 (1998).
Joki et al., *Nat. Biotech.*, 19, 35 (2001).
Kandel, J. et al., *Cell*, 66, 1095–104 (1991).
Kim, Y. M. et al., *Cancer Res.* 60, 5410–5413 (2000).
Kumagai, H. et al., *Biochem. Biophys. Res. Commun.*, 177, 74–82 (1991).
Lawn et al., Nucleic Acids Res., 9, 6103 (1981).

Maeshima, Y. et al., *J. Biol. Chem.*, 275, 23745–23750 (2000).
Maisonpierre et al., *Science*, 277, 55–60 (1997).
Martinsen et al., *Biotechnol. Bioeng.*, 33:79–89 (1989).
Moore et al., *J. Mol. Biol.*, 272, 336 (1997).
O'Reilly, M. S. et al. *Cell*, 88, 277–285 (1999).
O'Reilly, M. S. et al., *Science*. 285 1926–1928 (1999).
Pastan et al., *Cell*, 47:641 (1986).
Ramakrishnan, S. et al., *Cancer Res.*, 56, 1324–1330 (1996).
Read et al., *Nat. Biotech.*, 19, 29 (2001).
Rehn et al., *Proc. Natl. Acad. Sci. USA*, 98:1024 (2001).
Sambrook et al., *Molecular Cloning: A Laboratory Manual* (Cold Spring Harbor Laboratory Press, N.Y. 1989).
Simmons et al., *Science*, 276, 276 (1997).
Sipkins, D. A. et al. *Nat. Med.*, 4, 623–626 (1998).
Stemmer, *Nature*, 370:389 (1994).
Stemmer, *Proc. Natl. Acad. Sci. USA*, 91:10747 (1999).
Thorpe et al., *Monoclonal Antibodies in Clinical Medicine*, Academic Press, pp. 168–190 (1982).
Thorpe et al., *Cancer Res.*, 47:5924 (1987).
Viera et al., *Meth. Enzymol.*, 153, 3 (1987).
Vitetta et al., *Science*, 238:1098 (1987).
Waldmann, *Science*, 252: 1657 (1991).
Wild, R. et al., *Microvasc. Res.*, 59, 368–376 (2000).
Yokoyama, Y. et al., *Cancer Res.*, 60, 2190–2196 (2000).
Yokoyama, Y. and Ramakrishnan, S. (in communication).
Zhang et al., *Proc. Natl. Acad. Sci. USA*, 94:4504 (1997).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A composition consisting of a chimeric polypeptide comprising a peptide or polypeptide targeting moiety specific for endothelial cells linked to an endostatin polypeptide, wherein the targeting moiety is linked to the carboxy terminus of the endostatin polypeptide, and wherein the amino acid at position 125 in the endostatin polypeptide is not proline.

2. The composition of claim 1 wherein the targeting moiety binds to integrin on endothelial cells.

3. The composition of claim 2 wherein the targeting moiety comprises RGD, NGR, RGDNGR (SEQ ID NO:8), or NGRRGD (SEQ ID NO:9).

4. The composition of claim 2 wherein the targeting moiety binds to $\alpha_v\beta_3/\alpha_v\beta_5$ integrins.

5. The composition of claim 1 wherein the targeting moiety and the endostatin polypeptide are linked via a peptide bond.

6. The composition of claim 1 wherein the amino acid at position 125 is alanine, valine, leucine, isoleucine or methionine.

7. The composition of claim 1 further comprising a pharmaceutically acceptable diluent.

8. The composition of claim 1 wherein the targeting moiety is RGD.

9. A sustained release dosage form comprising the composition of claim 1.

10. The sustained release dosage form of claim 9 which comprises alginate beads.

11. A host cell transformed with recombinant DNA encoding a chimeric polypeptide consisting of a peptide or polypeptide targeting moiety specific for endothelial cells linked to an endostatin polypeptide, wherein the targeting moiety is linked to the carboxy terminus of the endostatin polypeptide, and wherein the amino acid at position 125 in the endostatin polypeptide is not proline.

12. A method to inhibit or prevent undesirable endothelial cell proliferation or migration, comprising: contacting a mammalian endothelial cell with an amount of a chimeric polypeptide comprising a peptide or polypeptide targeting moiety specific for endothelial cells linked to an endostatin polypeptide effective to inhibit or prevent undesirable endothelial cell proliferation or migration, wherein the targeting moiety is linked to the carboxy terminus of the endostatin polypeptide, and wherein the amino acid at position 125 in the endostatin polypeptide is not proline.

13. The method of claim 12 wherein the mammalian cell is a human cell.

14. The method of claim 12 wherein the composition comprises a RGD-containing peptide linked to endostatin.

15. A therapeutic method comprising: administering to a mammal having a condition characterized by undesirable endothelial cell proliferation or migration, a dosage from comprising an effective amount of a chimeric polypeptide comprising a peptide to polypeptide targeting moiety specific for endothelial cells linked to an endostatin polypeptide, wherein the targeting moiety is linked to the carboxy terminus of the endostatin polypeptide, and wherein the dosage form is a sustained release dosage form comprising alginate.

16. The method of claim 15 wherein the condition is cancer, diabetic retinopathy, macular degeneration, or restenosis.

17. The method of claim 15 wherein the condition is colon cancer.

18. The method of claim 15 wherein the condition is ovarian cancer.

19. The method of claim 15 wherein amino acid at position 125 of endostatin is not a proline.

20. The method of claim 19 wherein the amino acid at position 125 is alanine, valine, leucine, isoleucine or methionine.

21. The method of claim 12 or 15 wherein the targeting moiety is RGD, NGR, RGDNGR (SEQ ID NO:8), or NGRRGD (SEQ ID NO:9).

22. A composition comprising a chimeric polypeptide comprising a peptide or polypeptide targeting moiety specific for endothelial cells linked to a mutant endostatin with an amino acid substitution at position 125 or comprising a mutant endostatin with an amino acid substitution at position 125.

23. A host cell transformed with recombinant DNA encoding a chimeric polypeptide comprising a peptide or polypeptide targeting moiety specific for endothelial cells linked to a mutant endostatin with an amino acid substitution at position 125 or encoding a mutant endostatin with an amino acid substitution at position 125.

24. A method to inhibit or prevent undesirable endothelial cell proliferation or migration, comprising: contacting a mammalian endothelial cell with an amount of a chimeric polypeptide comprising a peptide or polypeptide targeting moiety specific for endothelial cells linked to a mutant endostatin with an amino acid substitution at position 125 or with an amount of a mutant endostatin with an amino acid substitution at position 125, effective to inhibit or prevent undesirable endothelial cell proliferation or migration.

25. A therapeutic method comprising: administering to a mammal having a condition characterized by undesirable endothelial cell proliferation or migration, a dosage from comprising an effective amount of a chimeric polypeptide comprising a peptide or polypeptide targeting moiety specific for endothelial cells linked to a mutant endostatin with an amino acid substitution at position 125.

* * * * *

UNITED STATES PATENT AND TRADEMARK OFFICE
CERTIFICATE OF CORRECTION

PATENT NO. : 6,825,167 B1
DATED : November 30, 2004
INVENTOR(S) : Yokoyama et al.

It is certified that error appears in the above-identified patent and that said Letters Patent is hereby corrected as shown below:

Title page,
Item [56], References Cited, OTHER PUBLICATIONS,
"Dawson, D.W., et al.," reference, delete "Factors:" and insert -- Factor : --, therefor.
"Folkman, J.," reference, delete "Evidencee" and insert -- Evidence --, therefor and delete "Dependent?" Jounal" and insert -- Dependent?", Jounal --, therefor.
"Friedlander, M. et al.," after "M." insert -- , --.
Item [57], ABSTRACT,
Line 2, delete "antiangiogeneic" and insert -- antiangiogenic --, therefor.

Signed and Sealed this

Nineteenth Day of April, 2005

JON W. DUDAS
*Director of the United States Patent and Trademark Office*

SEQUENCE LISTING

```
<160> NUMBER OF SEQ ID NOS: 14

<210> SEQ ID NO 1
<211> LENGTH: 30
<212> TYPE: DNA
<213> ORGANISM: Artificial Sequence
<220> FEATURE:
<223> OTHER INFORMATION: A Primer

<400> SEQUENCE: 1
ggggaattcc acagccaccg cgacttccag                                        30

<210> SEQ ID NO 2
<211> LENGTH: 35
<212> TYPE: DNA
<213> ORGANISM: Artificial Sequence
<220> FEATURE:
<223> OTHER INFORMATION: A Primer

<400> SEQUENCE: 2
ggggcggccg cctacttgga ggcagtcatg aagct                                  35

<210> SEQ ID NO 3
<211> LENGTH: 48
<212> TYPE: DNA
<213> ORGANISM: Artificial Sequence
<220> FEATURE:
<223> OTHER INFORMATION: A Primer

<400> SEQUENCE: 3
ggggaattcc atcatcatca tcatcatcac agccaccgcg acttccag                    48

<210> SEQ ID NO 4
<211> LENGTH: 32
<212> TYPE: DNA
<213> ORGANISM: Artificial Sequence
<220> FEATURE:
<223> OTHER INFORMATION: A Primer

<400> SEQUENCE: 4
ggggcggccg ccttggaggc agtcatgaag ct                                     32

<210> SEQ ID NO 5
```

-continued

```
<211> LENGTH: 38
<212> TYPE: DNA
<213> ORGANISM: Artificial Sequence
<220> FEATURE:
<223> OTHER INFORMATION: A Primer

<400> SEQUENCE: 5
gggaattcag aggagatcac agccaccgcg acttccag                              38

<210> SEQ ID NO 6
<211> LENGTH: 44
<212> TYPE: DNA
<213> ORGANISM: Artificial Sequence
<220> FEATURE:
<223> OTHER INFORMATION: A Primer

<400> SEQUENCE: 6
ggggcggccg cctaatctcc tctcttggag gcagtcatga agct                       44

<210> SEQ ID NO 7
<211> LENGTH: 30
<212> TYPE: DNA
<213> ORGANISM: Artificial Sequence
<220> FEATURE:
<223> OTHER INFORMATION: A Primer

<400> SEQUENCE: 7
ggggaattcc acagccaccg cgacttccag                                       30

<210> SEQ ID NO 8
<211> LENGTH: 6
<212> TYPE: PRT
<213> ORGANISM: Artificial Sequence
<220> FEATURE:
<223> OTHER INFORMATION: Targeting moiety

<400> SEQUENCE: 8

Arg Gly Asp Asn Gly Arg
 1               5

<210> SEQ ID NO 9
<211> LENGTH: 6
<212> TYPE: PRT
<213> ORGANISM: Artificial Sequence
<220> FEATURE:
<223> OTHER INFORMATION: Targeting moiety

<400> SEQUENCE: 9

Asn Gly Arg Arg Gly Asp
 1               5

<210> SEQ ID NO 10
<211> LENGTH: 4
<212> TYPE: PRT
<213> ORGANISM: Artificial Sequence
<220> FEATURE:
<223> OTHER INFORMATION: Negative control

<400> SEQUENCE: 10

Arg Gly Glu Ser
 1

<210> SEQ ID NO 11
<211> LENGTH: 4
<212> TYPE: PRT
<213> ORGANISM: Artificial Sequence
<220> FEATURE:
```

-continued

```
<223> OTHER INFORMATION: RGD Peptide

<400> SEQUENCE: 11

Arg Gly Asp Ser
1

<210> SEQ ID NO 12
<211> LENGTH: 14
<212> TYPE: PRT
<213> ORGANISM: Artificial Sequence
<220> FEATURE:
<223> OTHER INFORMATION: RGD Peptide

<400> SEQUENCE: 12

His His His His Gly Gly Gly Arg Gly Asp Gly Gly Gly Cys
1               5                   10

<210> SEQ ID NO 13
<211> LENGTH: 7
<212> TYPE: PRT
<213> ORGANISM: Artificial Sequence
<220> FEATURE:
<223> OTHER INFORMATION: RGD Peptide

<400> SEQUENCE: 13

Cys Gly Gly Gly Arg Gly Asp
1               5

<210> SEQ ID NO 14
<211> LENGTH: 4
<212> TYPE: PRT
<213> ORGANISM: Artificial Sequence
<220> FEATURE:
<223> OTHER INFORMATION: A peptide

<400> SEQUENCE: 14

Arg Gly Ala Asp
1
```